(12) United States Patent
Layer

(10) Patent No.: US 7,347,862 B2
(45) Date of Patent: Mar. 25, 2008

(54) APPARATUS FOR POSITIONING A MEDICAL INSTRUMENT RELATIVE TO A PATIENT

(76) Inventor: James H. Layer, 10427 SW. 49th Pl., Fort Lauderdale, FL (US) 33328

( * ) Notice: Subject to any disclaimer, the term of this patent is extended or adjusted under 35 U.S.C. 154(b) by 606 days.

(21) Appl. No.: 10/428,069

(22) Filed: May 2, 2003

(65) Prior Publication Data

US 2003/0208207 A1 Nov. 6, 2003

Related U.S. Application Data

(60) Provisional application No. 60/441,127, filed on Jan. 21, 2003, provisional application No. 60/427,572, filed on Nov. 20, 2002, provisional application No. 60/376,848, filed on May 2, 2002.

(51) Int. Cl.
*A61B 19/00* (2006.01)
(52) U.S. Cl. ...................................... 606/130
(58) Field of Classification Search ................ 606/130, 606/205, 206–210
See application file for complete search history.

(56) References Cited

U.S. PATENT DOCUMENTS

| | | | |
|---|---|---|---|
| 3,262,452 A | 7/1966 | Hardy et al. | |
| 3,338,235 A | 8/1967 | Gordon | |
| 3,359,583 A | 12/1967 | Strube | |
| 3,480,002 A | 11/1969 | Flaherty et al. | |
| 3,481,494 A | 12/1969 | Walischmiller | |
| 3,835,854 A | 9/1974 | Jewett | |
| 3,888,362 A | 6/1975 | Fletcher et al. | |
| 3,913,582 A | 10/1975 | Sharon | |
| 4,005,782 A | 2/1977 | Crockett | |
| 4,024,959 A | 5/1977 | Gruner | |
| 4,058,001 A | 11/1977 | Waxman | |
| 4,089,293 A | 5/1978 | Lyons | |
| 4,150,326 A | 4/1979 | Engelberger et al. | |
| 4,233,991 A | 11/1980 | Bradley et al. | |
| 4,248,213 A | 2/1981 | Landre | |
| 4,485,453 A | 11/1984 | Taylor | |
| 4,490,022 A | 12/1984 | Reynolds | |

(Continued)

FOREIGN PATENT DOCUMENTS

CA 664403 6/1963

(Continued)

*Primary Examiner*—Michael J. Hayes
*Assistant Examiner*—Victor Nguyen
(74) *Attorney, Agent, or Firm*—Michael J. Keller; Loit & Friedland, P.A.

(57) ABSTRACT

An apparatus for receiving and positioning a medical instrument relative to the body of a patient when the instrument is positioned partially within the body or completely outside the body. The apparatus comprises a housing and a motor assembly positioned within the housing. The motor assembly includes a motor and a first medical instrument engaging member operatively connected to the motor and moveable relative to the housing in response to the operation of the motor. A second medical instrument engaging member cooperates with the first medical instrument engaging member to drive the medical instrument within the housing when the medical instrument is positioned within the housing between the first and second medical instrument engaging members. The apparatus can form a portion of a trocar, a structure secured to a trocar or a structure that is free of a connection to a trocar or other medical instrument support.

4 Claims, 36 Drawing Sheets

U.S. PATENT DOCUMENTS

| | | | |
|---|---|---|---|
| 4,517,963 A | 5/1985 | Michel | |
| 4,592,352 A | 6/1986 | Patil | |
| 4,744,362 A | 5/1988 | Grundler | |
| 4,750,487 A | 6/1988 | Zanetti | |
| 4,764,944 A | 8/1988 | Finlayson | |
| 4,766,465 A | 8/1988 | Takahashi | |
| 4,791,934 A | 12/1988 | Brunnett | |
| 4,846,173 A | 7/1989 | Davidson | |
| 4,860,732 A | 8/1989 | Hasegawa et al. | |
| 4,863,133 A | 9/1989 | Bonnell | |
| 4,945,914 A | 8/1990 | Allen | |
| 4,979,949 A | 12/1990 | Matsen, III et al. | |
| 5,045,054 A | 9/1991 | Hood et al. | |
| 5,050,608 A | 9/1991 | Watanabe et al. | |
| 5,078,140 A | 1/1992 | Kwoh | |
| 5,084,010 A | 1/1992 | Plaia et al. | |
| 5,086,401 A | 2/1992 | Glassman et al. | |
| 5,090,401 A | 2/1992 | Schwieker | |
| 5,093,978 A | 3/1992 | Binder | |
| 5,112,340 A | 5/1992 | Krenkel et al. | |
| 5,119,817 A | 6/1992 | Allen | |
| 5,184,601 A | 2/1993 | Putman | |
| 5,240,011 A | 8/1993 | Assa | |
| 5,318,541 A | 6/1994 | Viera et al. | |
| 5,354,314 A | 10/1994 | Hardey et al. | |
| 5,397,323 A | 3/1995 | Taylor et al. | |
| 5,417,210 A | 5/1995 | Funda et al. | |
| 5,494,034 A | 2/1996 | Schlondorff et al. | |
| 5,515,478 A | 5/1996 | Wang | |
| 5,524,180 A | 6/1996 | Wang et al. | |
| 5,553,198 A | 9/1996 | Wang et al. | |
| 5,555,897 A | 9/1996 | Lathrop, Jr. et al. | |
| 5,571,072 A * | 11/1996 | Kronner | 600/102 |
| 5,599,348 A | 2/1997 | Gentelia et al. | |
| 5,657,429 A | 8/1997 | Wang et al. | |
| 5,754,741 A | 5/1998 | Wang et al. | |
| 5,766,126 A | 6/1998 | Anderson | |
| 5,779,623 A | 7/1998 | Bonnell | |
| 5,797,835 A | 8/1998 | Green | |
| 5,814,038 A | 9/1998 | Jensen et al. | |
| 5,820,623 A | 10/1998 | Ng | |
| 5,827,241 A | 10/1998 | Douk et al. | |
| 5,855,583 A | 1/1999 | Wang et al. | |
| 5,876,325 A | 3/1999 | Mizuno et al. | |
| 5,878,193 A | 3/1999 | Wang et al. | |
| 5,907,664 A | 5/1999 | Wang et al. | |
| 5,976,156 A | 11/1999 | Taylor et al. | |
| 5,997,471 A | 12/1999 | Gumb et al. | |
| 6,022,325 A | 2/2000 | Siczek et al. | |
| 6,024,695 A | 2/2000 | Taylor et al. | |
| 6,035,228 A | 3/2000 | Yanof et al. | |
| 6,080,181 A | 6/2000 | Jensen et al. | |
| 6,102,850 A | 8/2000 | Wang et al. | |
| 6,106,511 A | 8/2000 | Jensen | |
| 6,132,368 A | 10/2000 | Cooper | |
| 6,201,984 B1 | 3/2001 | Funda et al. | |
| 6,231,526 B1 | 5/2001 | Taylor et al. | |
| 6,231,565 B1 | 5/2001 | Tovey et al. | |
| 6,246,200 B1 | 6/2001 | Blumenkranz et al. | |
| 6,290,675 B1 | 9/2001 | Vujanic et al. | |
| 6,306,146 B1 | 10/2001 | Dinkler | |
| 6,346,072 B1 | 2/2002 | Cooper | |
| 6,371,952 B1 | 4/2002 | Madhani et al. | |
| 6,406,472 B1 | 6/2002 | Jensen et al. | |
| 6,409,735 B1 | 6/2002 | Andre et al. | |
| 6,413,264 B1 | 7/2002 | Jensen et al. | |
| 6,434,329 B1 | 8/2002 | Dube et al. | |
| 6,451,027 B1 | 9/2002 | Cooper et al. | |
| 6,461,372 B1 * | 10/2002 | Jensen et al. | 606/205 |
| 6,463,361 B1 | 10/2002 | Wang et al. | |
| 6,620,174 B2 | 9/2003 | Jensen et al. | |
| 2001/0018591 A1 | 8/2001 | Brock et al. | |
| 2002/0032451 A1 | 3/2002 | Tierney et al. | |
| 2002/0042606 A1 | 4/2002 | Castaneda et al. | |
| 2002/0072736 A1 | 6/2002 | Tierney et al. | |
| 2002/0133174 A1 | 9/2002 | Charles et al. | |
| 2003/0040758 A1 | 2/2003 | Wang et al. | |
| 2003/0109957 A1 | 6/2003 | Sanchez et al. | |
| 2003/0195661 A1 | 10/2003 | Wang et al. | |
| 2003/0216715 A1 | 11/2003 | Moll et al. | |

FOREIGN PATENT DOCUMENTS

| | | |
|---|---|---|
| DE | 10015510 | 10/2001 |
| EP | 0326768 | 8/1989 |
| FR | 2 715 597 | 8/1995 |
| GB | 2094590 | 9/1982 |
| JP | 59-157715 | 9/1984 |
| JP | 60-231208 | 11/1985 |
| NL | 1000685 | 12/1996 |
| RU | 0603577 | 4/1978 |
| WO | WO 00/30557 | 6/2000 |

* cited by examiner

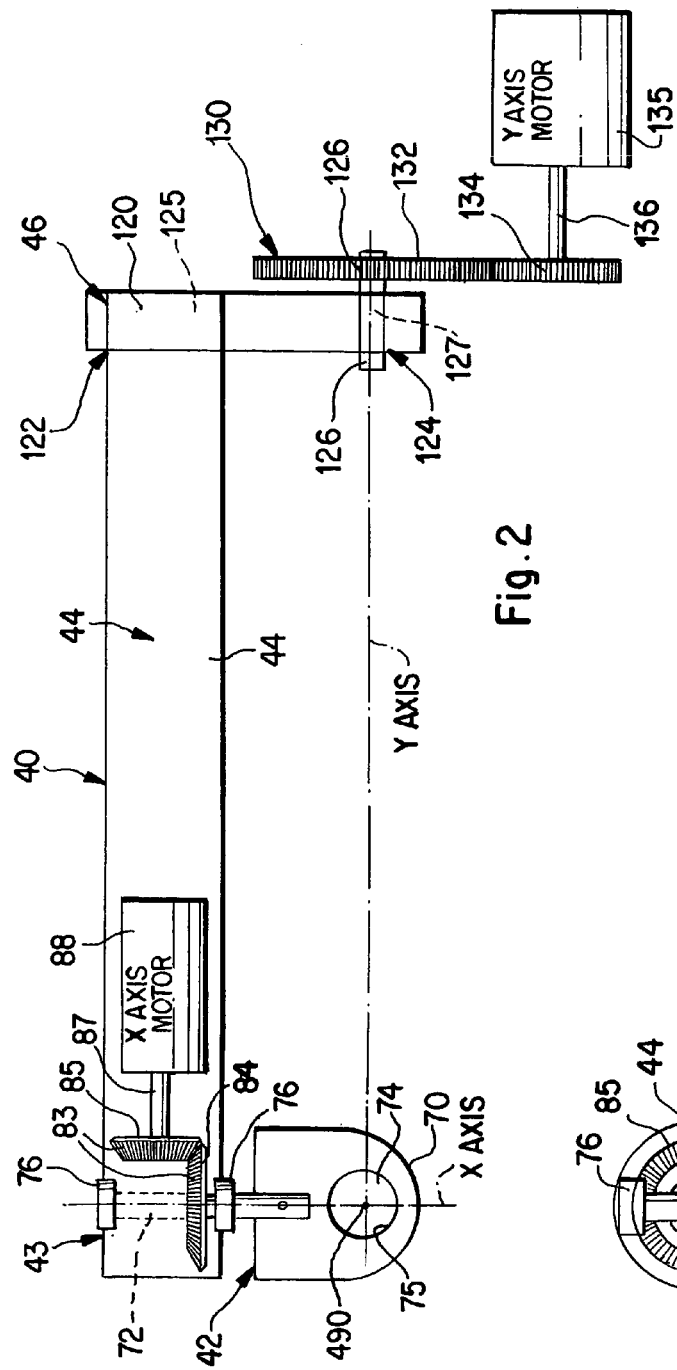
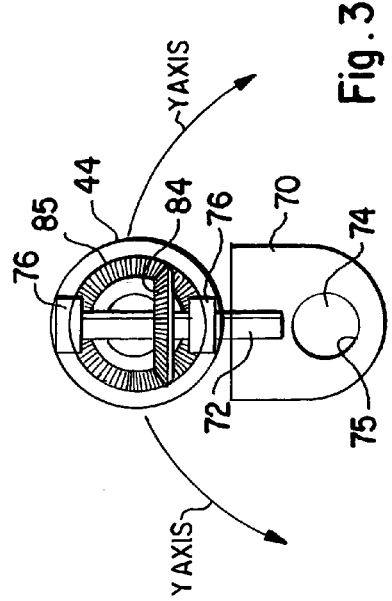
Fig. 2
Fig. 3

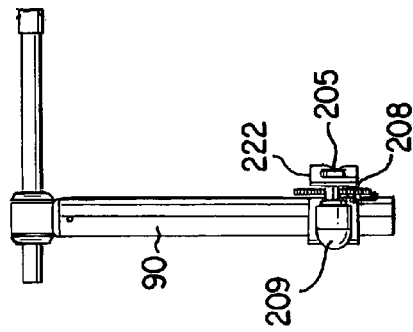
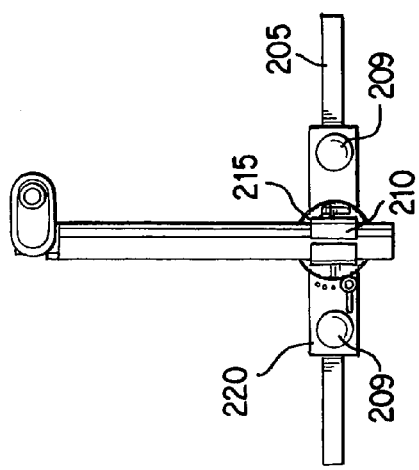
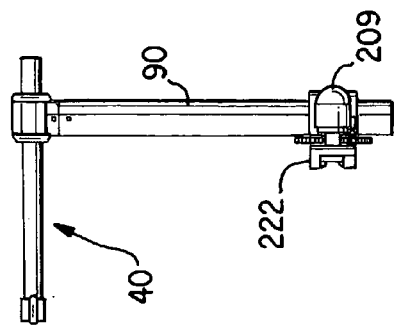
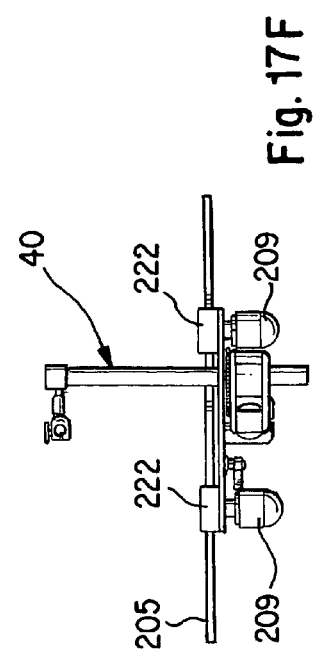

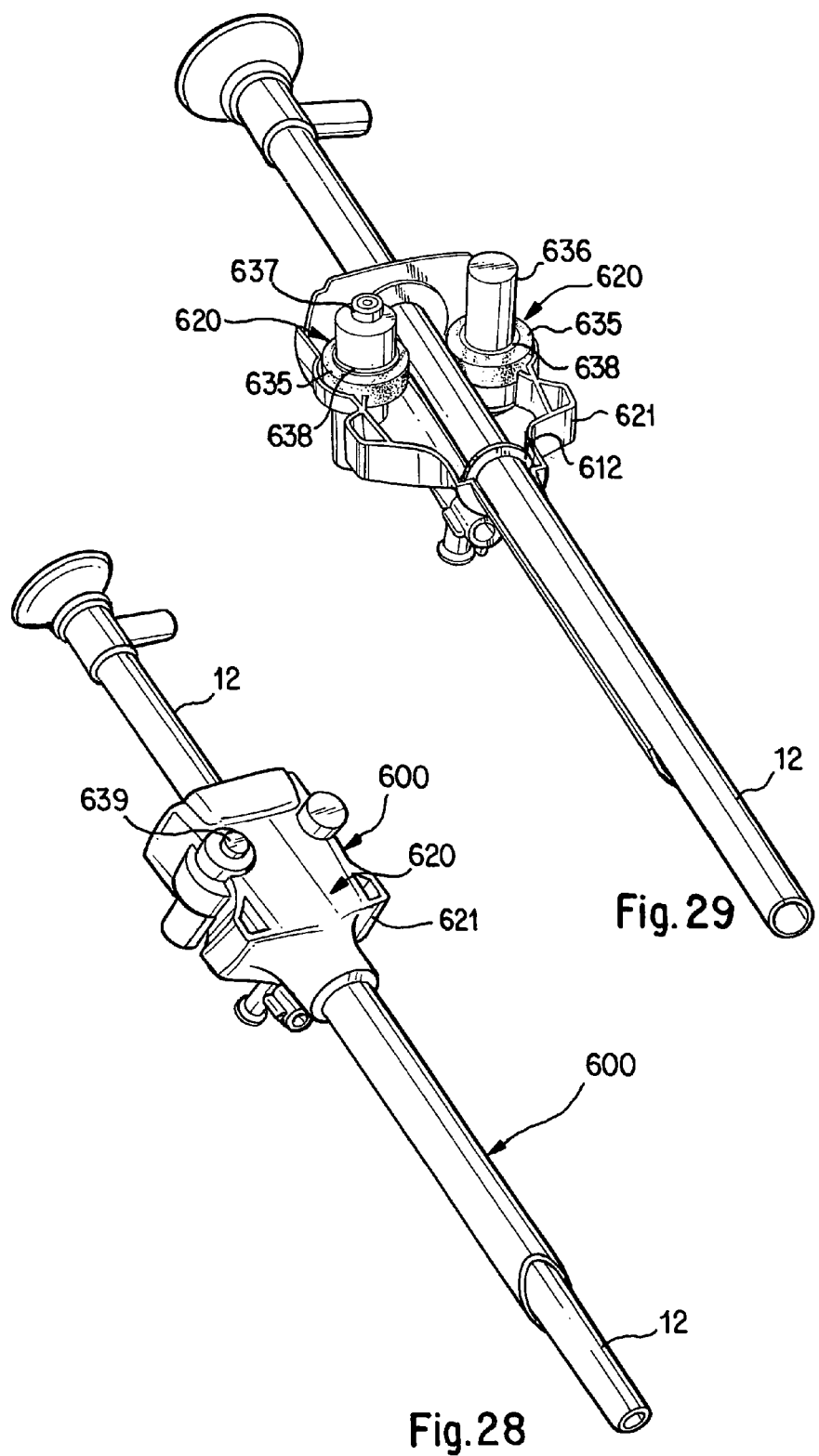

US 7,347,862 B2

APPARATUS FOR POSITIONING A MEDICAL INSTRUMENT RELATIVE TO A PATIENT

This application claims the benefit of and incorporates by reference co-pending U.S. provisional application Ser. No. 60/376,848 filed May 2, 2002, co-pending U.S. provisional application Serial No. 60/427,572 filed Nov. 20, 2002, and co-pending U.S. provisional application Ser. No. 60/441,127 filed Jan. 21, 2003.

FIELD OF THE INVENTION

The present invention relates to an apparatus for positioning a surgical instrument during a surgical procedure, and more particularly to an apparatus for accurately positioning and repositioning an instrument, such as an endoscope, during a surgical procedure, such as laparoscopic surgery.

BACKGROUND OF THE INVENTION

Accurate and precise manipulation of surgical instruments at or near a surgical site is required during any surgical procedure. However, this is especially true for minimally invasive endoscopic surgical procedures, such as laparoscopic surgery, in which the doctor has a limited amount of room to maneuver the instrument. While the following discussion relates to laparoscopies, it is equally applicable to any for endoscopic procedure.

As is well-known, laparoscopic surgery (laparoscopy) is a procedure in which surgical instruments and an endoscope, referred to normally as a laparoscope, are inserted into the abdominal cavity of a patient through a hollow tubular device positioned within a small incision in the patient. These tubular devices are commonly referred to as trocars or cannulas and remain in the incision throughout the procedure. The laparoscope comprises an illuminated tube and an optical system that is inserted through the tubular device in the abdominal wall for examining the abdominal cavity. The optical system includes an image receiving lens that can be connected to a remotely positioned monitor.

Endoscopes are presently hand held or positioned with complicated and expensive devices. They are constantly being repositioned to obtain the best view. When hand supported throughout the surgical procedure, the laparoscope must be constantly manually manipulated by the surgeon, assistant surgeon, and/or a scrub nurse in order to direct it at the target of the surgery. This process ties up one hand of the surgeon or assistant surgeon, if either holds the scope. The scrub nurses have other tasks to perform, and holding the scope interferes with performing these tasks. It is also difficult for the surgeon to direct others to position the scope for the best view. When the surgeon does not hold the scope, it is often misdirected. This can result in injury to the patient and delays in the conclusion of the surgery.

Mechanical support of a laparoscope has been provided conventionally using a robotic arm. However, these arms face many of the same problems encountered when the laparoscope is held by hand. For example, the movements of the laparoscope can be in the wrong direction and/or to an improper depth within the body. Additionally, these robotic systems can take up too much space in the operating room and require someone to constantly monitor and operate it. This unnecessarily ties up one of the members of the operating team and can contribute to crowding of the operation site. Additionally, many of the conventional systems allow the laparoscopes to bend and twist within the body, thereby stretching the incision.

Moreover, some conventional positioning systems typically attach to the instrument or laparoscope at a point above the trocar, which is approximately 4 to 8 inches above the abdomen wall. This creates a geometrical challenge to maintain an X and Y-axis pivot point at the incision of the abdominal wall and a stable image. Typically the above mentioned complicated and expensive mechanical linkages that extend over the patient are used to accomplish this positioning without any shaking of the image.

SUMMARY OF THE INVENTION

The present device provides an apparatus for securely positioning an endoscope relative to the body of a patient. An aspect of the present invention includes a trocar for receiving and positioning a medical instrument. The trocar comprises a housing and a motor assembly positioned within said housing. The motor assembly includes a motor, a first medical instrument engaging member operatively connected to the motor and moveable relative to the housing, and a second medical instrument engaging member. When the medical instrument is positioned within said housing between the first and second medical instrument engaging members, the operation of the motor causes the first and second medical instrument engaging members to move the medical instrument in one of multiple directions.

Another aspect of the present invention includes an apparatus for moving a medical instrument in at least one direction. The apparatus comprises an elongated trocar and a drive assembly releasably secured to the elongated trocar. The drive assembly comprises a housing including an opening for receiving the medical instrument, at least one motor and at least one drive roller operatively coupled to said motor. The rotation of the drive roller causes the medical instrument to move within the trocar.

A further aspect of the present invention includes an apparatus for positioning a medical instrument relative to the body of a patient including a medical instrument drive assembly comprising a motor, a drive roller operatively coupled to said motor, an idler roller for cooperating with said drive roller for moving the medical instrument and a housing. The housing comprises a first housing portion supporting one of the drive roller and the idler roller and a second housing portion supporting the other of the drive roller and the idler roller. The second housing portion is moveable relative to said first housing portion. In an embodiment, the second housing portion pivots relative to the first housing portion.

Another aspect of the present invention includes a powered trocar for engaging and positioning a medical instrument relative to the body of a patient. The powered trocar comprises a first portion for housing a drive assembly including at least one motor and at least one drive roller mechanically coupled to the motor. The drive roller includes a friction material for contacting and moving the medical instrument. The powered trocar also includes a second portion extending from the first portion for positioning proximate the patient. This second portion includes an opening through which the medical instrument extends from the trocar.

The present invention overcomes disadvantages of the prior art devices.

Generally, the present invention includes a medical instrument positioning apparatus that provides for controlled adjustment of the medical instrument, such as a laparoscope, relative to the body of the patient in a direction parallel to the longitudinal axis of the medical instrument and/or in a direction that encircles the longitudinal axis of the medical instrument. At least one embodiment of the present invention utilizes the tension provided by the skin at the incision site to hold one or more medical instruments, thereby reducing the number of instruments needed at the surgical site. The present invention maintains the orientation of the laparoscope so that it will not twist or tip over while being moved relative to the body of the patient. Additionally, the arrangement of the aspects of the present invention can be more compact and less cumbersome than conventional medical instrument positioners. Additionally, the apparatus and systems of the present invention can be operated using a single hand and/or a foot.

These and other features and advantages of the present invention will be apparent from the preferred embodiment described in the following detailed description and illustrated in the accompanying drawings.

BRIEF DESCRIPTION OF THE DRAWINGS

FIG. 2 is a cross section of a C-shaped arm taken along the line 2-2 of FIGS. 1A and 1B;

FIG. 3 is an end view of the C-shaped arm taken proximate a trocar adapter rotated ninety degrees about the X and Y axes relative to FIG. 2;

FIGS. 17A-17F illustrate different view of the securing system of FIG. 12;

FIGS. 28 and 29 illustrate the trocar with motor housing of FIG. 27 including an inserted instrument;

FIG. 35 is a side view of the trocar motor housing of FIG. 34 with an endoscopic instrument extending there through;

DETAILED DESCRIPTION OF THE PREFERRED EMBODIMENT

Figure 1A:
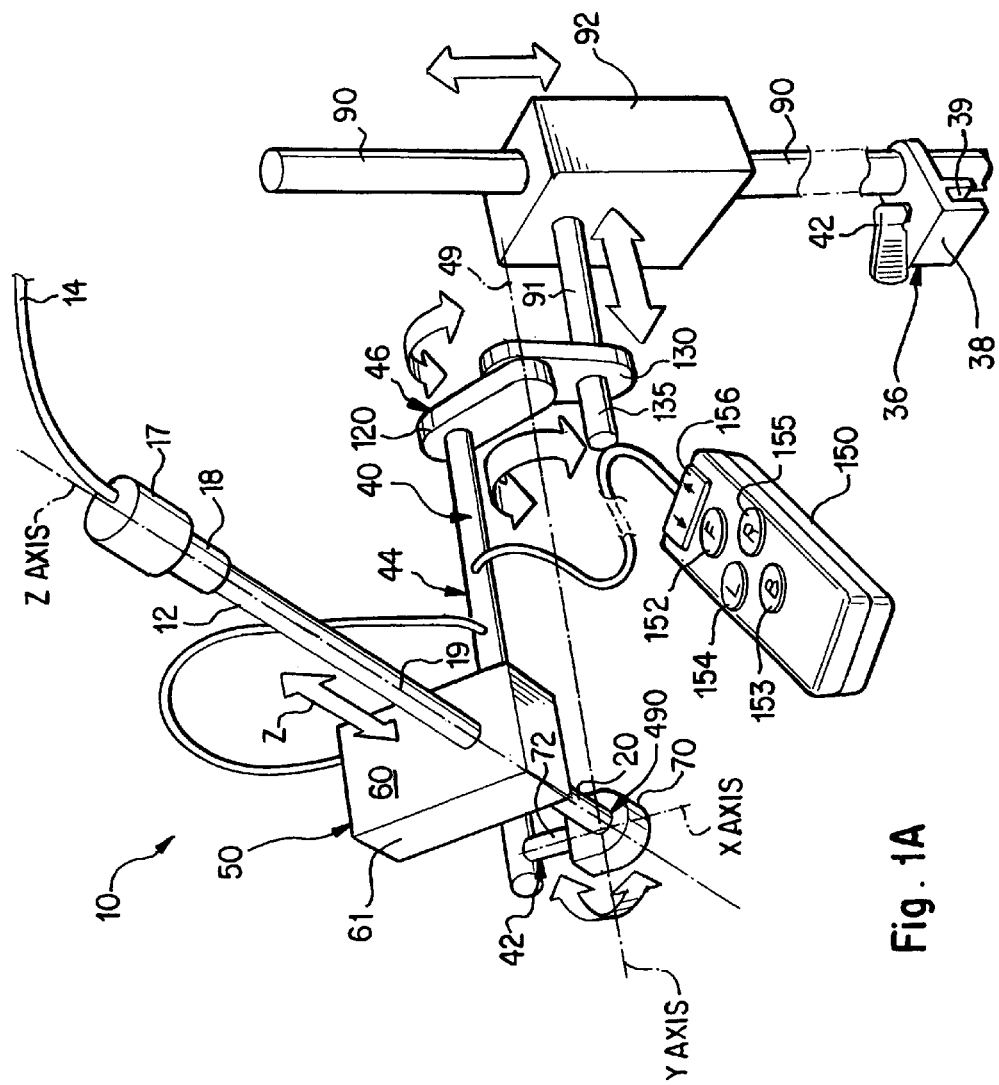
FIG. 1A is an isometric view of a first embodiment of an apparatus for positioning a medical instrument according to the present invention.
Figure 1B:
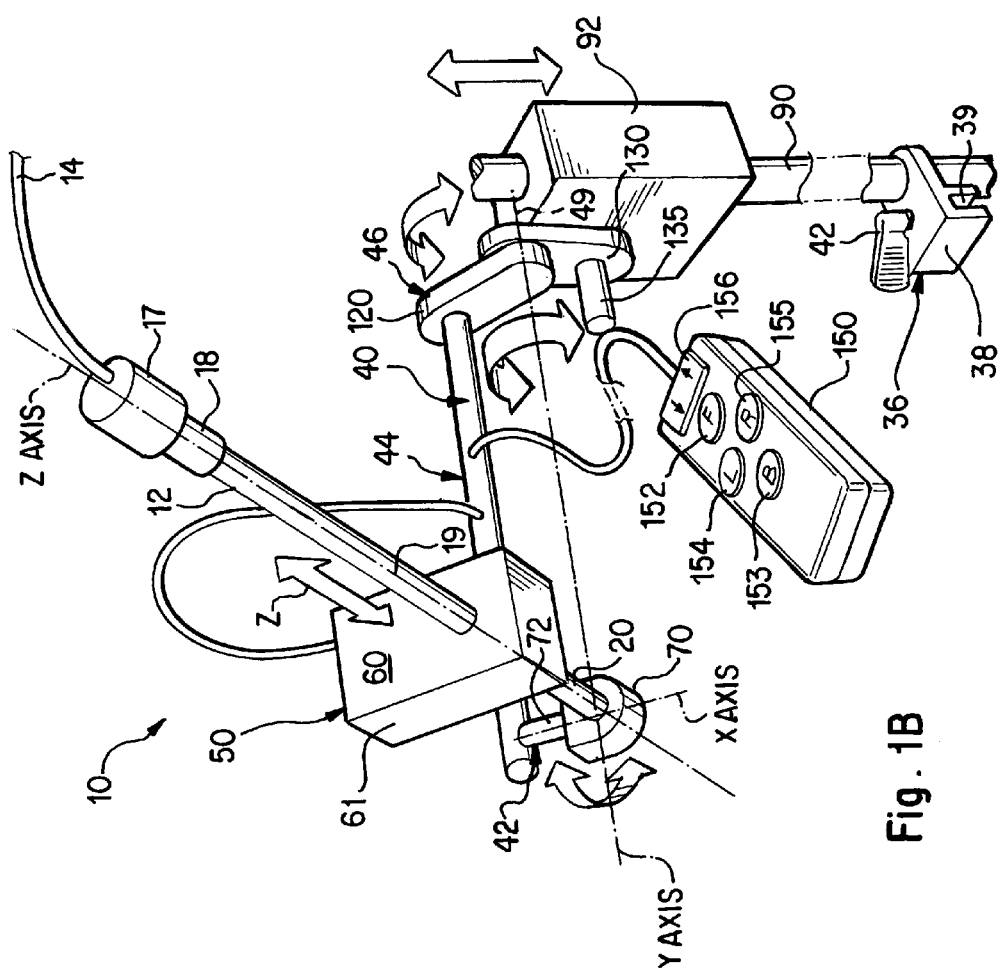
FIG. 1B is an isometric view of a second embodiment of an apparatus for positioning a medical instrument according to the present invention.

FIGS. 1A and 1B show an apparatus 10 for supporting and positioning a conventional medical instrument 12 relative to an operating table that has an equipment mounting member or a horizontally extending edge to which the apparatus 10 can be secured. Embodiments of such an apparatus 10 are discussed in U.S. Provisional Patent Application No. 60/376,848, which is hereby incorporated by reference.

Known medical instruments 12 include graspers, forceps, cauterizing devices, endoscopes and all other instruments used in endoscopic procedures. In other embodiments, the medical instrument 12 can include a drill, a trocar or other piercing device. For ease of explanation and clarity, the following description of the present invention will discuss the apparatus 10 and how it positions and supports an endoscope, specifically a laparoscope. However, the following discussion is not limited to laparoscopes. Instead, it is equally applicable to other endoscopes and other medical equipment that require stable support and accurate positioning during medical procedures.

Figure 4:
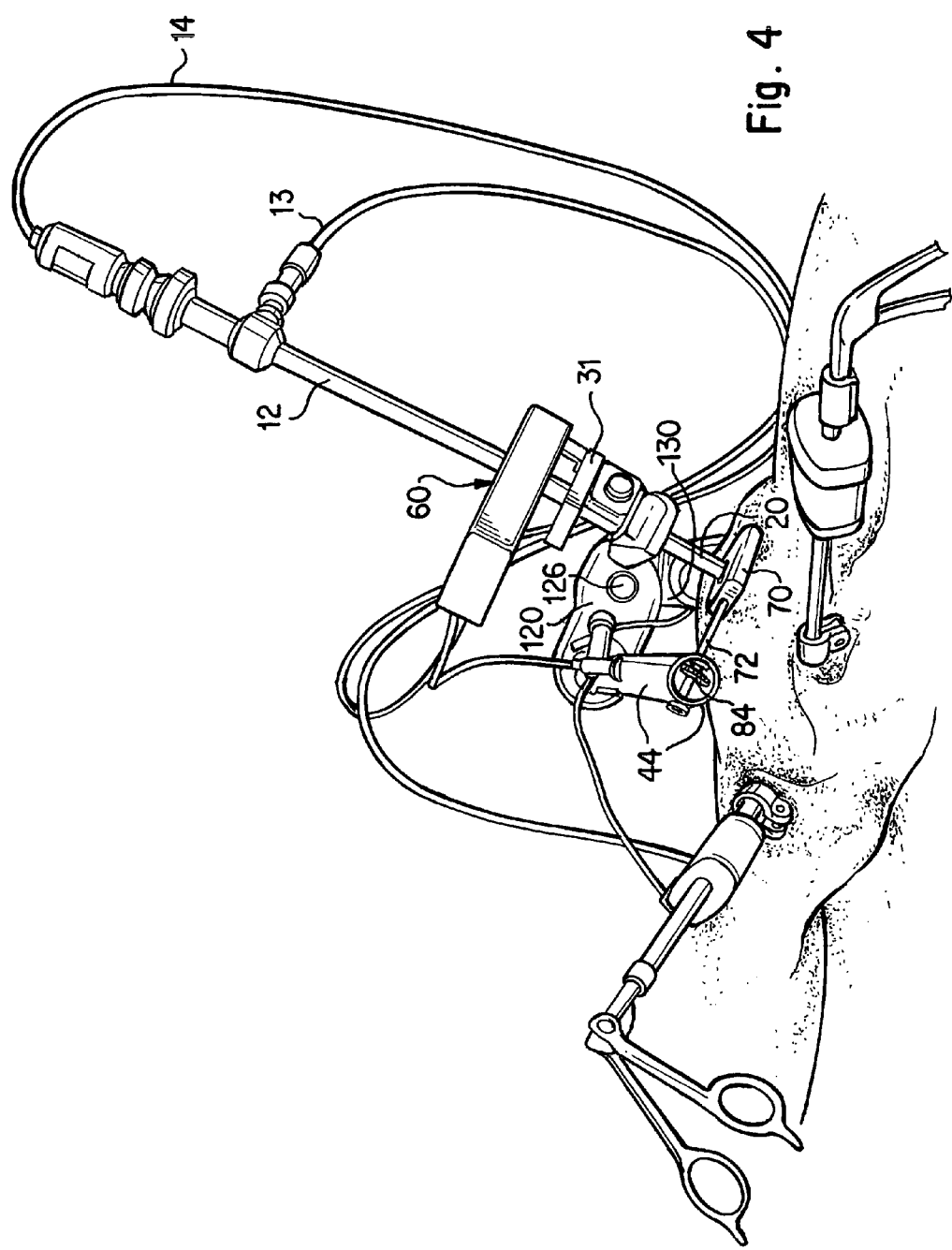
FIG. 4 is a side isometric view of the apparatus illustrated in FIGS. 1A and 1B.
Figure 5:
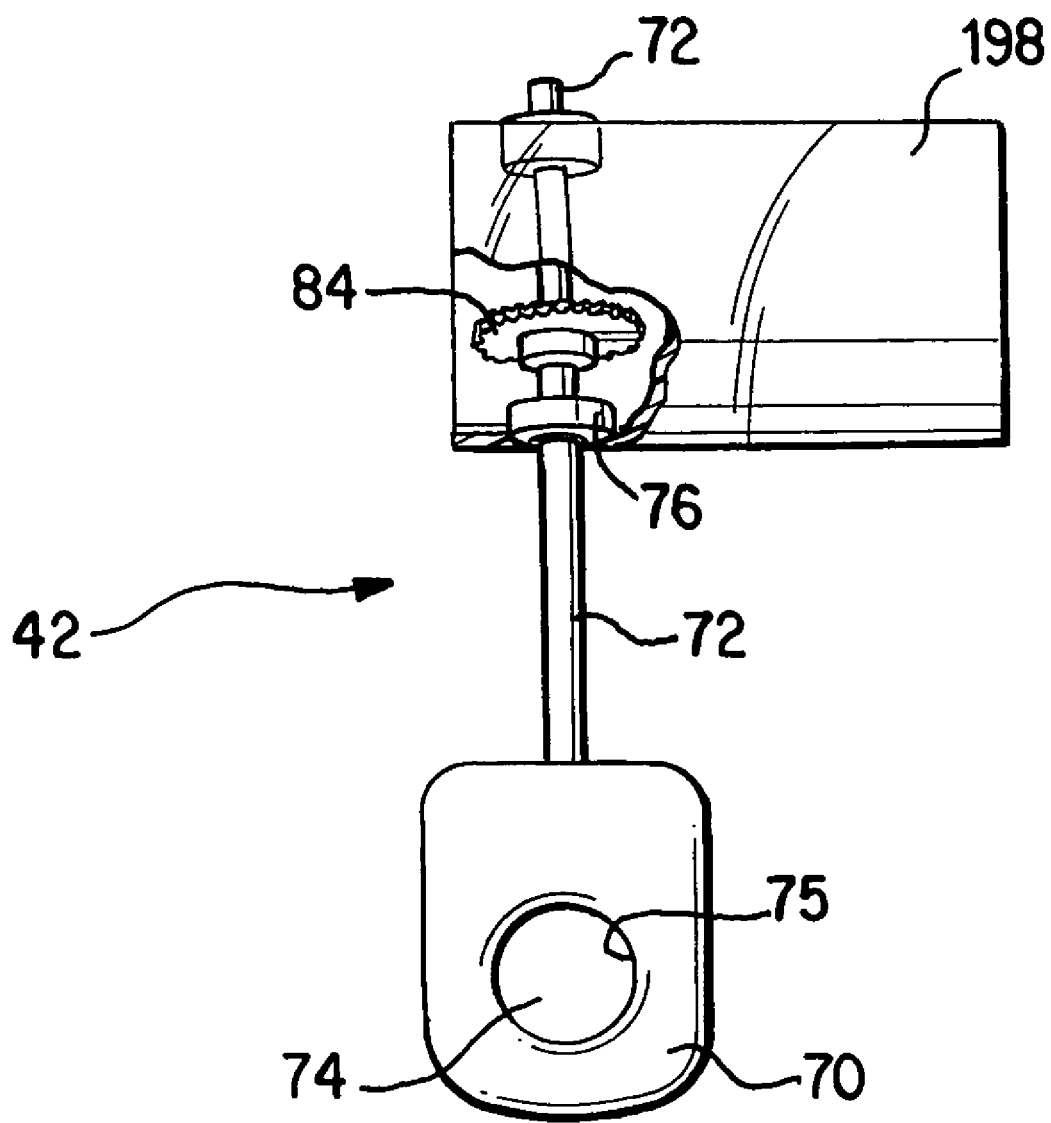
FIG. 5 illustrates a portion of the trocar adapter and a portion of a middle section of the C-shaped arm.
Figure 9:
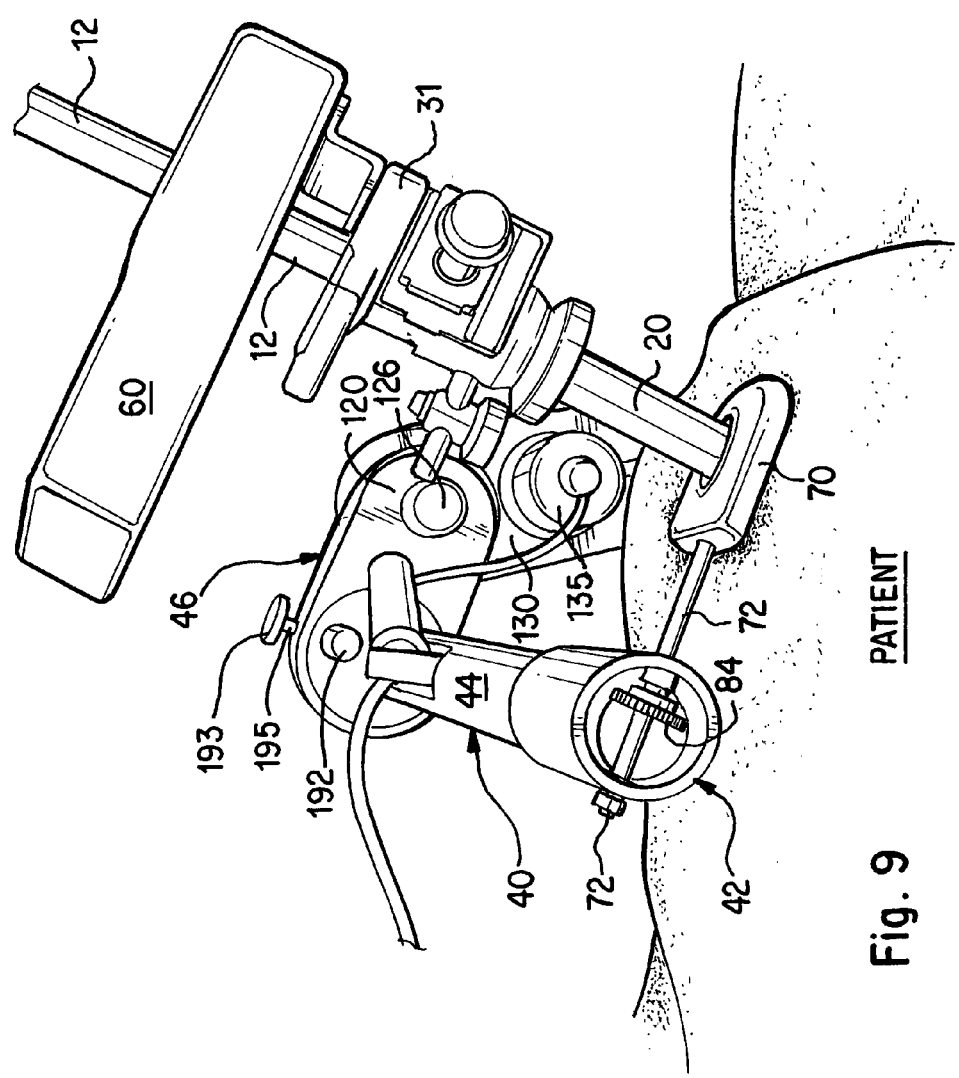
FIG. 9 is a side view of the apparatus illustrated in FIGS. 1-8.

The laparoscope 12 illustrated in FIGS. 1A, 1B and 9 can be any known conventional laparoscope that includes an eyepiece 18 mounted on the end of a viewing tube 19. The viewing tube 19 also includes a video camera 17 that is connected to a video monitor (not shown) that is located proximate the surgical site. The laparoscope 12 also includes a light source (not shown) that is connected to a light cable 13 that transmits light from the light source to an end of the light cable 13 positioned in the abdominal cavity. The light is directed out of the end of the tube 19 for illuminating the body cavity. The body cavity is then viewed by a video camera 17 connected to the monitor by a connecting cable 14 (FIG. 4).

Apparatus 10 includes a stanchion 90 that has a base 36, a securing system including a base clamp 38 and a jaw 39 for securing the apparatus to a support such as a support rail or edge of an operating table as shown in FIG. 1A. Manual turning of a lever 42 screws a clamp shaft for moving the jaw 39 relative to a base member that is positioned on an opposite side of the support from the jaw 39. However, any known manner of securing an endoscope support system relative to an operating table may be used. One such way is disclosed in U.S. Pat. No. 5,571,072 that is incorporated herein by reference.

As shown in FIGS. 1A, 1B and 2, the apparatus 10 includes a "C" shaped arm 40 that operates as a positioning system and that rotates relative to the patient. The C-shaped arm 40 also rotates relative to the vertical stanchion 90, as well as, moving linearly relative to the stanchion 90. An elongated member 91 connects the C-shaped arm 40 to a stanchion housing 92 supported on the stanchion 90 as shown in FIG. 1A. The housing 92 receives the elongated member 91 and the vertical stanchion 90. The housing 92 is also moveable relative to both the stanchion 90 and the elongated member 91. As a result, the housing 92 and the C-shaped arm 40 can be positioned at any point along the length of the stanchion 90. This stanchion length can be in either a horizontal direction (X axis) or a vertical direction (Y axis). Additionally, the C-shaped arm 40 can be positioned a distance away from the housing 92. This distance can be adjusted by moving elongated member 91 in or out of the housing 92 in a direction perpendicular to the length of the stanchion 90. In an alternative embodiment illustrated in FIG. 1B, the C-shaped arm 40 is secured directly to the stanchion housing 92. Welds or fasteners, such as screws or bolts, can be used to secure the C-shaped arm 40 directly to the stanchion.

As discussed below with respect to drive system housing 61, the housing 92 can include two or more powered rubber pinch rollers that frictionally engage the stanchion 90 and move the housing 92 along the length of the stanchion 90. Similarly, two or more powered rubber pinch rollers can also be used to move the elongated member 91 into and out of the housing 92. As with the stanchion 90, the rollers apply compressive pressure to the elongated member 91 and move the elongated member 91 in the direction that they rotate. A driven rubber pinch roller and a rubber idler roller could be used in place of the two or more driven rubber rollers.

In another alternative embodiment, the housing 92 can be moved manually relative to stanchion 90 and member 91 via known linear ball bearings, bushings or other bearing surfaces through which the stanchion 90 and elongated member 91 extend. In this embodiment, the housing 92 includes a known friction lock that can be manually applied to the stanchion 90 When the housing is at the proper height along stanchion 90 such as friction member 123 discussed below. Manually applied friction locks, like friction member 123, can also be used to secure the housing 92 along the elongated member 91.

In any of the discussed embodiments, the elongated member 91 can include a hollow tube with an internal lumen carrying an elongated drive shaft 136 (FIG. 2). Alternatively, the elongated member 91 can rotate freely within the pinch rollers or linear bearings about the axis along which the elongated member 91 moves relative to the housing 92.

Figure 12:
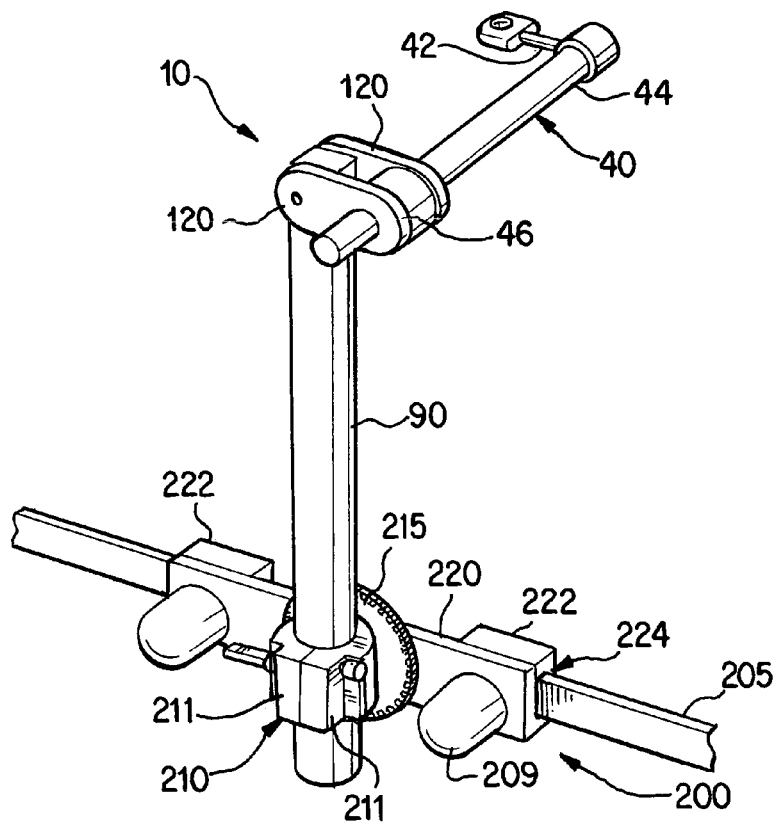
FIG. 12 illustrates a securing system for attaching a stanchion to a rail of an operating room table and permitting controlled degree-by-degree movement of the stanchion relative to the operating table and a patient.
Figure 13:
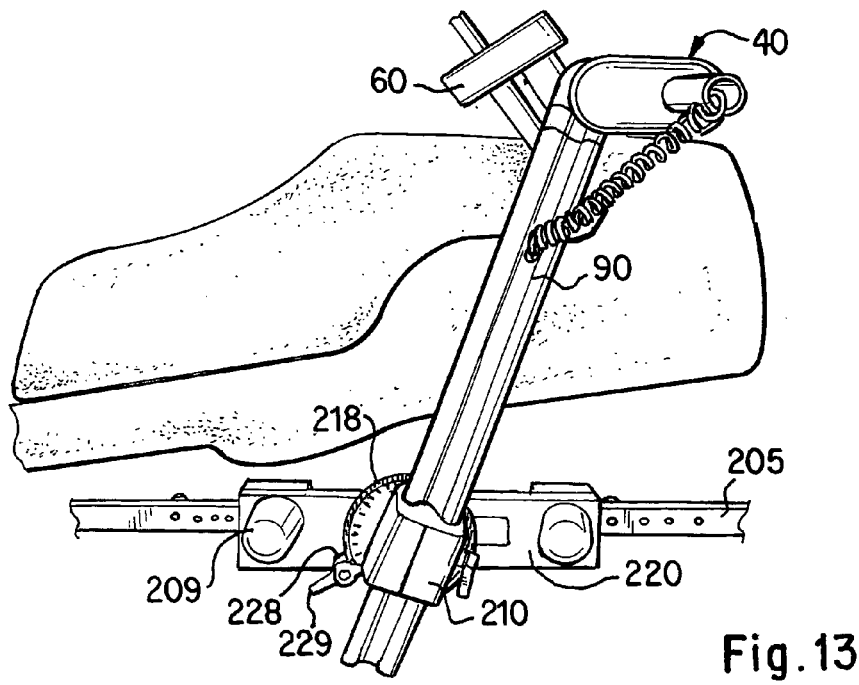
FIG. 13 illustrates the securing system of FIG. 12 secured to a rail.
Figure 12A:
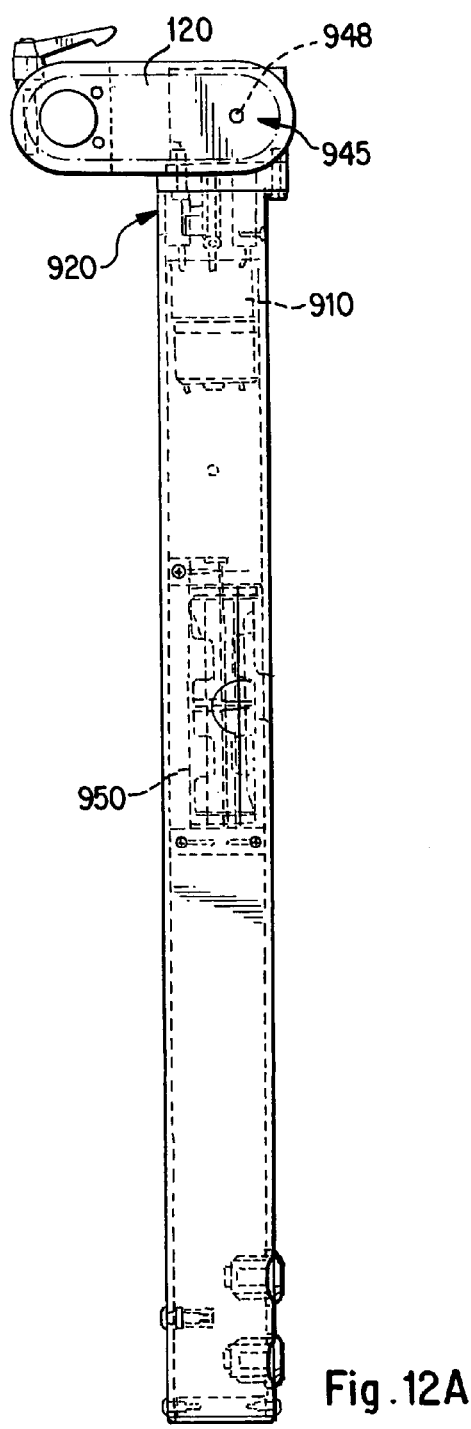
FIGS. 12A and 12B illustrate a motor for rotating a positioning system located within a vertical stanchion.
Figure 12B:
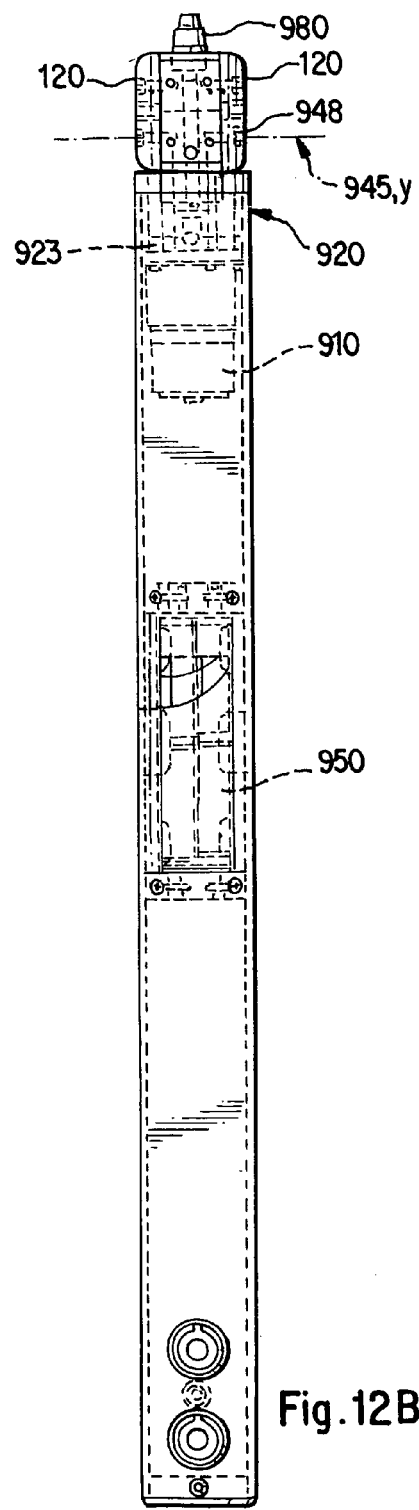

FIGS. 12-17 illustrate an additional embodiment of a securing system 200 that can be used with any of the embodiments of the medical instrument support and positioning apparatus 10 discussed herein to securely position such an apparatus on a rail 205 of a surgical table during a medical procedure. In these embodiments, as well as others disclosed herein, the C-shaped arm 40 can be rotated about the Y-axis by the operation of a motor 910 within the stanchion 90. As illustrated in FIGS. 12A and 12B, the stanchion 90 can include the motor 910 and a power source 950. As with any of the embodiments discussed herein, the power source 950 can include a DC power source such as batteries or an AC power source. The motor 910 includes a drive shaft 923 that drives a gear system 920 with an output shaft(s) connected to the links 120. A conventional worm drive gear system including a worm gear and a driven gear, or a beveled gear system including a driven gear and a follower gear can be used to transfer the motion of the drive shaft to the links 120. This motion will cause the links 120 and the remainder of the C-shaped arm 40 to pivot (rotate) about a pivot axis 945 that extends substantially parallel to, and coextensive with, the Y-axis. A pin 948 can be positioned within the links 120 at a first end for rotatably coupling the links 120 to the stanchion 90. A clamp 980 can be included for releasably receiving the middle section 44 within the links 120.

Figure 16:
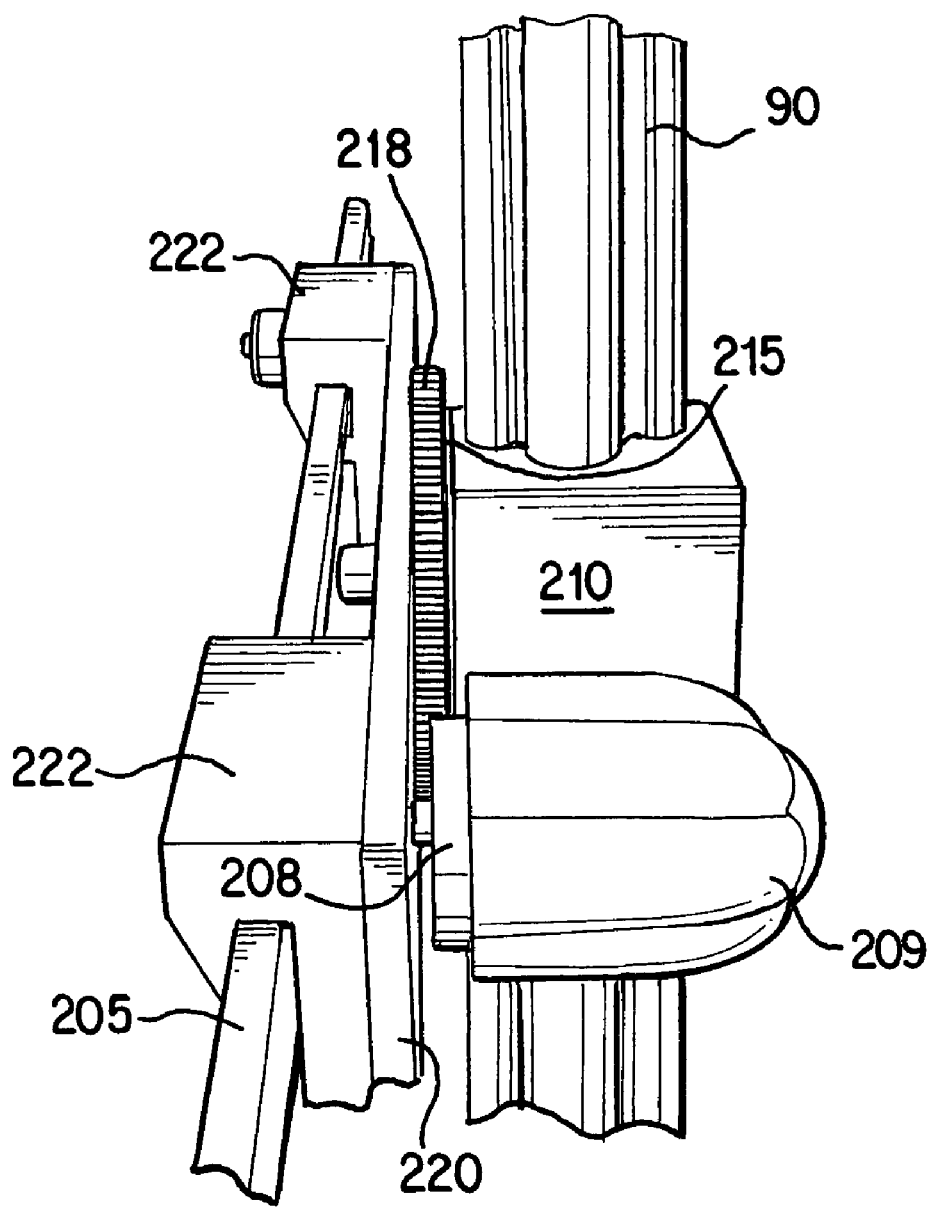
FIG. 16 illustrates a support plate and brackets for attaching the securing system to the rail.
Figure 17B:
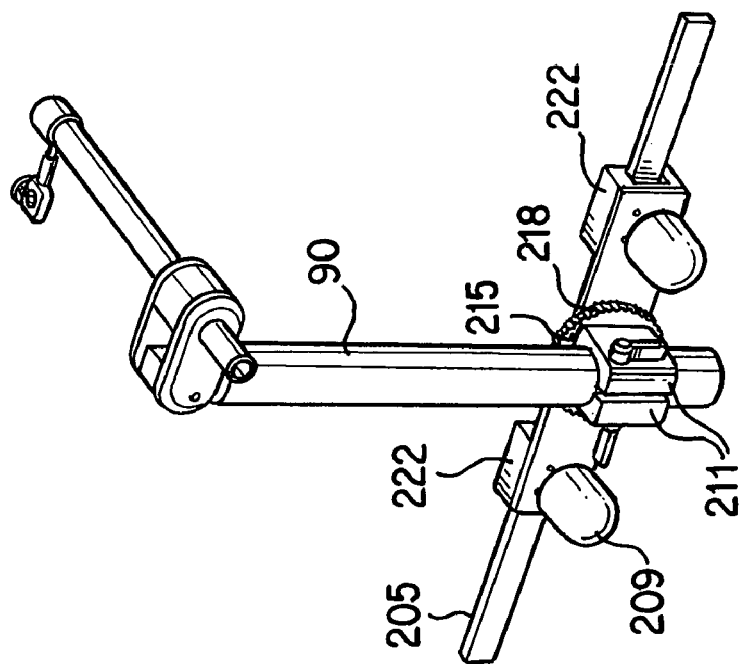
Figure 17A:
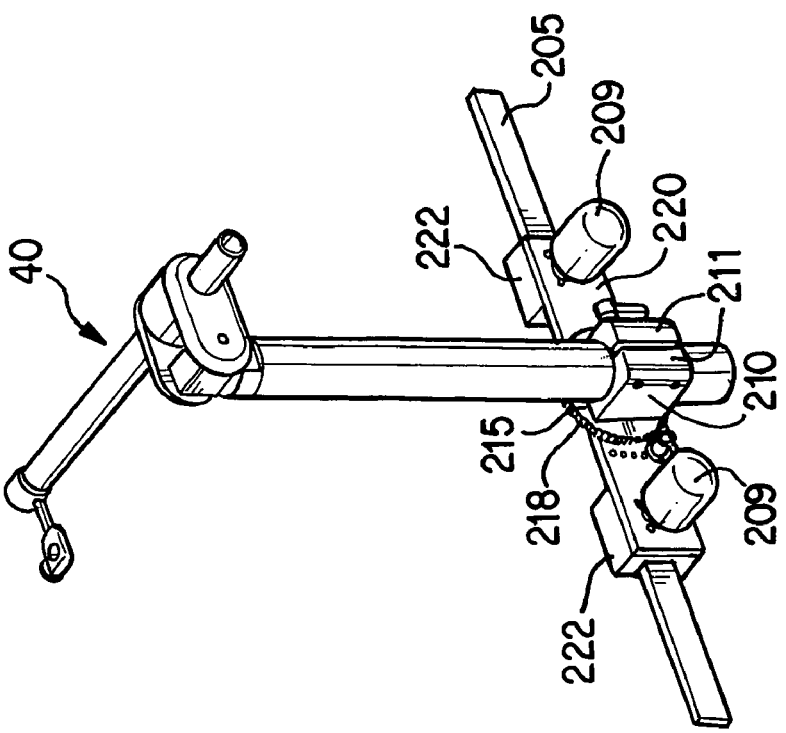

The securing system 200 also permits rotation of the apparatus 10 about the rail 205. The securing system 200 includes a rail mounting plate 220 and a pair of brackets 222 that receive the rail 205 and positioning of the C-shaped arm 40. Each bracket 222 includes an opening 224 for receiving a portion of the rail 205. In one embodiment, the opening 224 is slid over the rail 205 so that the only motion that the brackets can achieve relative to the rail 205 is a sliding motion along the length of the rail 205. The brackets 222 can be closed blocks or include openings along their rear face (facing the operating table). As shown in FIGS. 16 and 17(e), the plate 205 is frictionally secured against sliding (longitudinal) movement relative to the rail 205 by a pair of stopping members 208 that are advanced through the plate 220 and into frictional engagement with the rail 205. When the grasping members 209 of the stopping members 208, such as knobs, are rotated, the stopping members 208 are rotated into engagement with the rail 205 or disengagement from the rail. As can be understood, this will depend on the direction of rotation. Other known ways of advancing the stopping members 208 into engagement with the rail 205 can also be used. These other known ways include the use of controlled motors.

Figure 14:
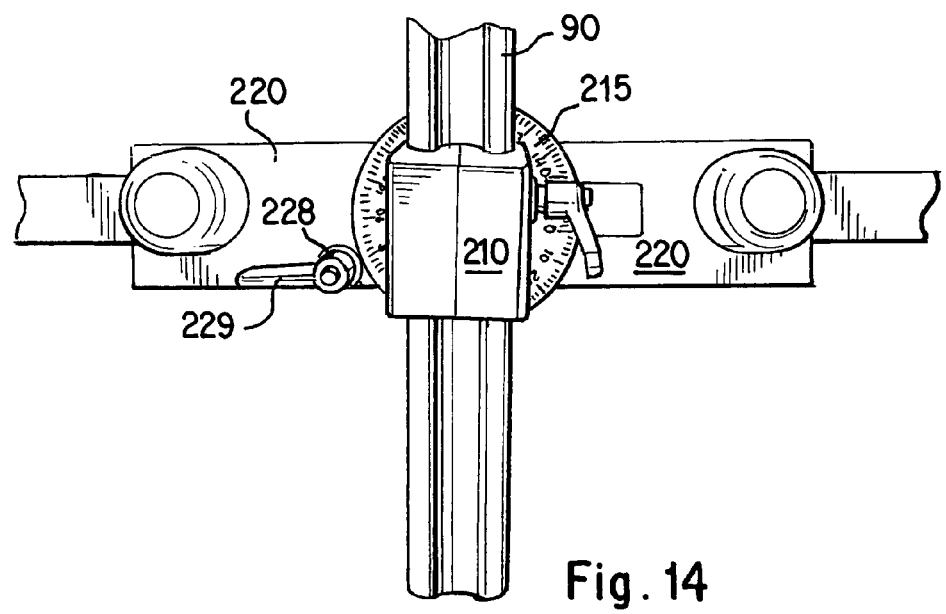
FIG. 14 is an enlarged view of a portion of FIG. 13.
Figure 15:
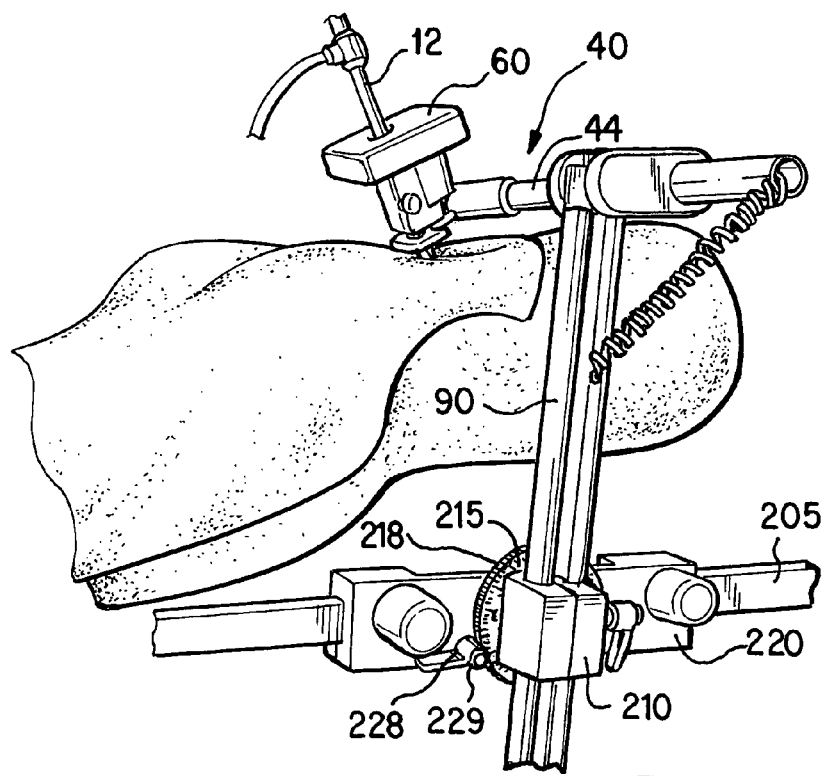
FIG. 15 is a perspective view of the securing system of FIG. 12.

The securing system 200 also includes a clamping bracket 210 for receiving the vertical stanchion 90. As illustrated in FIG. 12, the clamping bracket 210 includes first and second sections 211 that are locked together to securely hold the vertical stanchion 90 and prevent movement of the stanchion 90 relative to the bracket 210. The bracket 210 is mounted to a rotatable disk 215 that is secured to an associated positioning gear 218 having a plurality of teeth. The positioning gear 218 is rotatably secured within a bearing positioned within plate 220 (see FIG. 16). As shown in FIGS. 14 and 15, a cooperating locking gear 228 is located on the plate 220 for engaging with the teeth of the positioning gear 218. Both gears 218, 228 can be driven by hand or by an associated motor. The locking gear 228 is secured to a handle 229 that when turned to a locking position holds and prevents rotational motion of both the locking gear 228 and the positioning gear 218 with which locking gear 228 is engaged. As a result, the stanchion 90 is prevented from rotating relative to the rail 205. In an alternative embodiment, the rotation and braking of the desired, predetermined rotation of the stanchion 90 can be achieved by the controlled operation and braking of a conventional drive motor.

The tubular C-shaped arm 40 of any of the above-discussed embodiments has a first end section 42, a second end section 46 and a middle section 44 that extends between the two end sections 42, 46. As shown in FIGS. 1A and 1B, the first end section 42 is distal the stanchion 90 relative to the second end section 46. The first end section 42 and the middle section 44 are tubular with open internal lumens extending along their length. The cross sections of these sections 42, 44 can be round, oval or rectangular. Other known shapes can also be used. The middle section 44 can be positioned along a portion of the patient's body during the medical procedure. In one embodiment, the middle section 44 should be positioned so that the pivot point 49 of the C-shaped arm 40 is at the skin surface of the patient. As illustrated in FIGS. 1A, 1B and 2, the first end section 42 and the second end section 46 extend substantially perpendicular to the length of the middle section 44. The second end section 46 includes a fixed link segment 120 or multiple fixed link segments 120 (FIG. 12) having a substantially rectangular shape with rounded ends.

During the medical procedure, a small incision is made in the abdomen of the patient and a trocar 20 (also referred to as a cannula) is introduced into the abdominal cavity through the incision in order to establish a pathway along which medical instruments such as the laparoscope 12 can enter the body. After the trocar 20 is properly positioned within the incision, the C-shaped arm 40 can be secured to the trocar 20 as discussed below.

As shown in FIGS. 1A, 1B and 9, the first end section 42 includes an endoscope positioning system 50 that adjusts the distance that the laparoscope 12 extends within the patient and a first angular component of the position of the laparoscope 12. The endoscope positioning system 50 is secured to the trocar 20 by a connector 31. As a result, relative movement between the endoscope positioning system 50 and the trocar 20 is prevented. As shown in FIGS. 4 and 9, the connector 31 extends between a Z-axis medical instrument drive assembly 60 and the trocar 20. As discussed herein, the medical instrument can include an endoscope. The connector 31 is secured to the laparoscopic drive assembly 60 in any conventional manner, such as by using threaded fasteners or brackets, that prevents their relative movement. The connector 31 is also secured to the trocar 20 in any known manner. In one embodiment, a closeable collar is secured around the end of the trocar 20 distal the patient. In an alternative embodiment, the end of the trocar 20 distal the patient is friction or force fitted within an opening in the end of the connector 31 opposite the drive assembly 60. Other known ways of coupling a tube to a housing can also be used.

Figure 7:
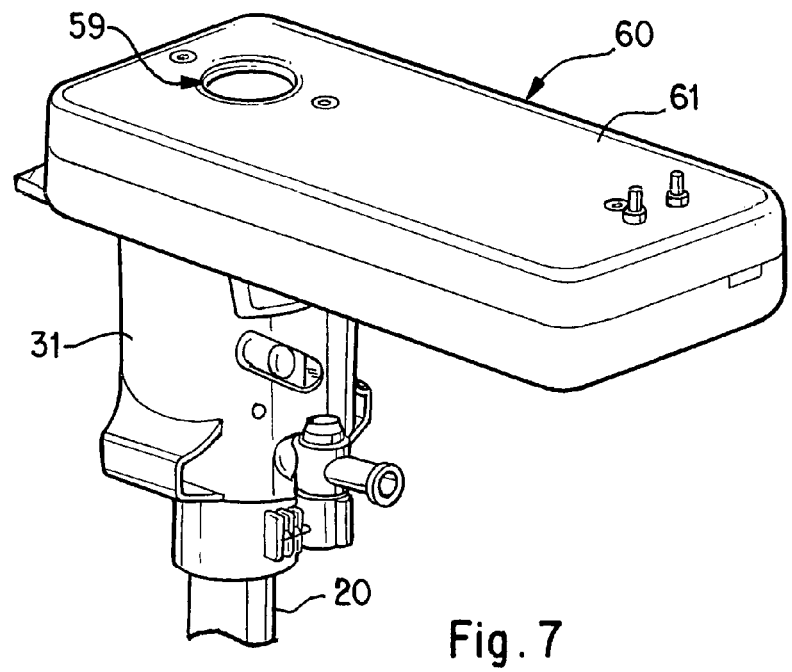
FIG. 7 is an isometric view of a motor housing according to the present invention.
Figure 8:
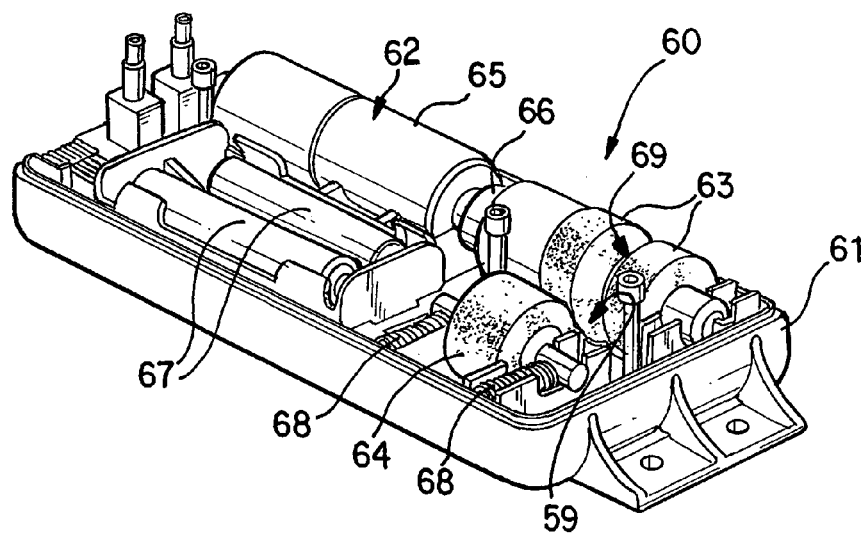
FIG. 8 is an isometric view of the motor housing of FIG. 7 with a cover removed.

As shown in FIGS. 7 and 8, the endoscope positioning system 50 includes the drive assembly 60 having a housing 61 with an endoscope receiving opening 59. The housing 61 is attached to the trocar 20 positioned within the abdominal cavity by the connector 31 as discussed above. The laparoscopic drive system housing 61 contains a motor assembly 62 that includes a driven rubber pinch roller 63 and a spring biased rubber idler roller 64. The rubber can include a silicon rubber having a durometer of between about forty and sixty. In one preferred embodiment, the durometer is about 50. Other known compressible materials having a high coefficient of friction and a durometer in the range of between about forty to sixty can be used in place of rubber for the rollers 63, 64. The rollers 63, 64 are not limited to the above-discussed durometers.

In one embodiment, the pinch roller 63 includes a V-shaped groove 69 for receiving the laparoscope 12 and providing pressure on it from multiple sides. A motor 65 drives the pinch roller 63 via a rotatable drive shaft 66. Batteries 67 or another electrical source powers the motor 65. The batteries 67 or other power source could also be located outside of housing 61. The idler roller 64 is biased into contact with the shaft of the laparoscope 12 by a set of coil springs 68 positioned between the idler roller 64 and a stationary object such as the inner wall of the housing 61. The biasing force applied by the springs 68 forces the idler roller 64 into contact with the laparoscope 12 and creates enough friction that the laparoscope 12 moves in the direction that the driven roller 63 rotates. The springs 68 and the V-groove 69 permit the rollers 63, 64 to accept any size laparoscopic shaft that will fit within the housing 61. It is contemplated that one or more springs could be used. Also, other types of springs can be used.

As the driven pinch roller 63 is operated, the laparoscope 12 is moved along a "Z" axis for advancing the laparoscope 12 into or withdrawing the scope from the abdomen via the trocar 20. As shown in the FIGS. 1A and 1B by the arrow labeled "Z", the Z axis extends in the direction that is perpendicular to the midline of the body and out of the paper of FIGS. 1A, 1B and 2. By advancing and withdrawing the laparoscope 12 using the drive assembly 60, the field of view of the laparoscope 12 and the image on the video monitor will change. For example, as the laparoscope 12 is advanced into the abdomen by the rotation of the driven pinch roller 63 in the direction of the patient, the practitioner can zoom in on the desired area within the body for a close up video image. Conversely, the retraction of the laparoscope 12 caused by the driven pinch roller 63 rotating away from the patient widens the field of view of the image on the monitor and permits the practitioner to view more of the body cavity.

Figure 8A:
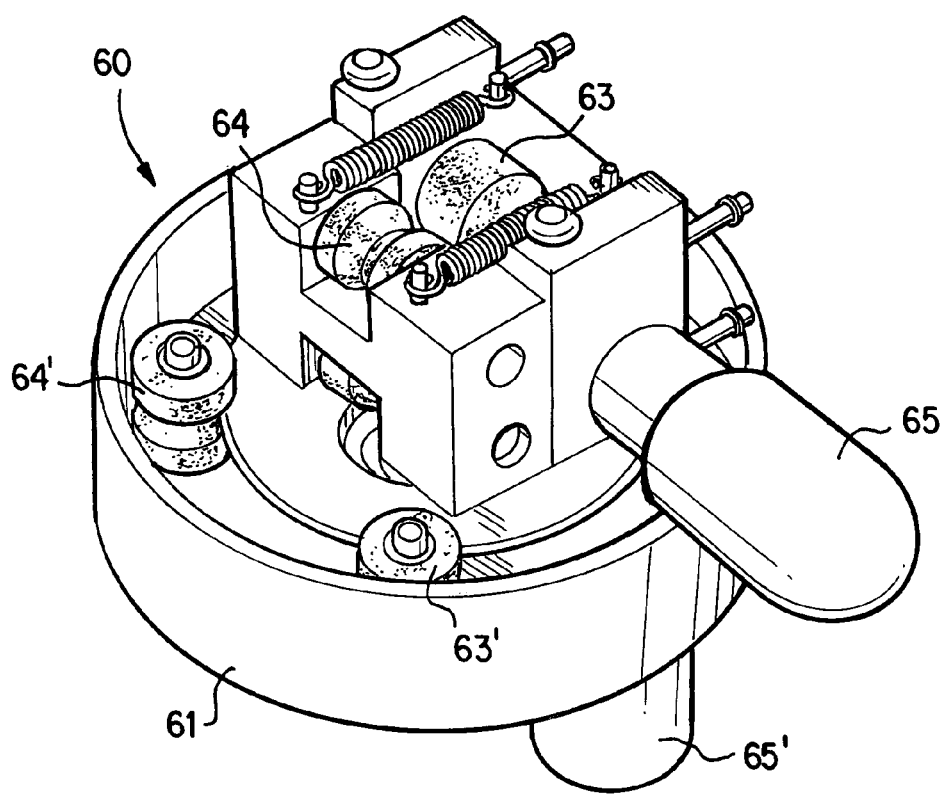
FIG. 8A is an isometric view of a motor housing include a pair of motors and two pairs of rollers that provide longitudinal and rotational motion to a medical instrument.

As illustrated in FIG. 8A, the housing 61 could also include a second motor assembly 62' and a second set of rollers 63', 64' that are similar to rollers 63, 64 for rotating the laparoscope 12 about its longitudinal axis. These rollers 63', 64' are oriented perpendicular to the rollers 63, 64 so that their axes of rotation extend parallel to the longitudinal axis of the laparoscope 12 when the laparoscope 12 is positioned between the rollers 63, 64. As a result, when the motor 65' rotates the driven roller 63', a rotatably secured plate 66' on which the drive assembly 60 is secured rotates about the longitudinal axis of the trocar (not shown). In response to the rotation of the plate 66', the laparoscope 12 secured between the grooves of the driven and spring-biased pinch rollers 63, 64 will rotate about its longitudinal axis.

In addition to the controlled movement of the laparoscope 12 along the Z axis, controlled rotational movement about an X axis can also be achieved. As shown in FIGS. 1A, 1B and 2, the first end section 42 includes a trocar adapter 70 and an adapter shaft 72 that connects the trocar adapter 70 to the middle section 44 of the C-shaped arm 40. As used herein, the term "adapter" includes the member(s) or system(s) that connects a trocar and/or drive assembly to the first end section 42 and supports the trocar and/or drive assembly relative to the first end section 42 such that the medical instrument 12 will move with the movement of the C-shaped arm 40. The adapter shaft 72 has a diameter of about 0.187 inch and a length of about 1.5 inch. The trocar adapter 70 and adapter shaft 72 cause the laparoscope 12, the camera 17 and the trocar 20 to rotate about the X axis so that the field of view or the location of the procedure can be altered. The direction of this rotational motion is shown in FIGS. 1A and 1B by the illustrated arrows. As seen in the figures, the trocar 20 is received within an opening 74 in the adapter 70. The inner surface 75 of the opening 74 acts as a bearing when the trocar 20 is being advanced into the adapter 70. The opening 74 can be sized to create a friction fit with the trocar 20 so that the trocar 20 will not unintentionally move relative to the adapter 70. As the adapter shaft 72 is rotated, the inner surface 75 transfers the rotational motion of the adapter 70 to the indwelling trocar 20, the laparoscope 12 and the camera 17. In one embodiment, the trocar adapter 70 is formed of a disposable plastic material. However, the trocar adapter 70 could also be formed of reusable, sterilizable materials including sterilizable plastics and sterilizable metals such as stainless steel.

As illustrated in FIGS. 11A-11D, the trocar adapter 70 can include a quick release clamping mechanism 140 that allows the trocar 20 to be quickly and removably secured within the adapter 70. In the embodiments illustrated in FIGS. 11A-11D, the trocar adapter 70 includes at least two sections 71' and 72' that are moveable relative to each other in order to create a larger opening for the introduction of the trocar 20 into the adapter 70. After the trocar 20 has been introduced into the adapter 70, the sections 71' and 72' are closed around the trocar 20 and secured to each other in order to hold the trocar 20 within the adapter 70. A first embodiment of the clamping mechanism 140, shown in FIG. 11A, includes a pivot member 141, such as a hinge, on one side of the adapter 70 and a fastener 142 for holding sections 71' and 72' together on the opposite side of the adapter 70. The fastener 142 can include a threaded member that engages threads located within the sections 71' and 72' or in a nut positioned in either section 71' or 72'. Alternatively, the fastener 142 could include a push-in fastener that frictionally and/or mechanically engages with sections 71' and 72' to prevent their relative movement and to prevent the longitudinal movement of the trocar 20 relative to the trocar adapter 70.

Figure 11A:
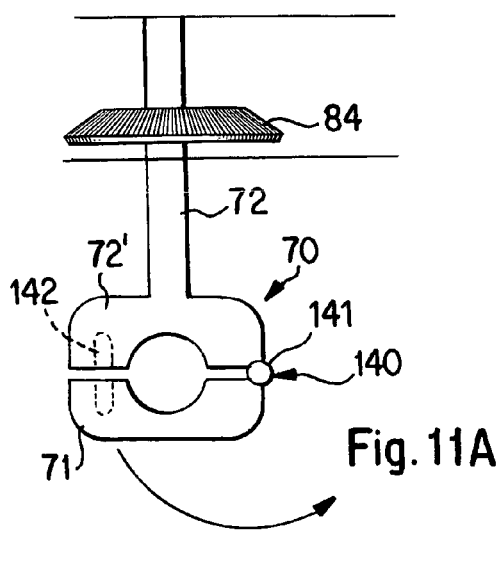
FIGS. 11A-11F illustrate different embodiments of a trocar adapter according to the present invention.
Figure 11D:
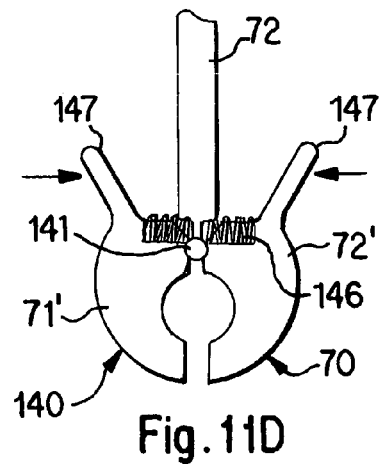
Figure 11B:
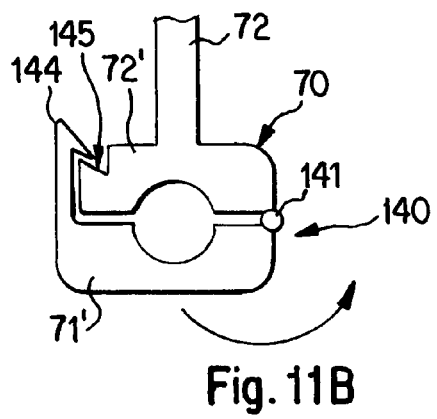

As shown in FIG. 11B, the clamping mechanism 140 can include a pivot hinge 141 connected to sections 71' and 72' for their relative movement. The clamping mechanism also includes a flexible catch hook 144 that extends from section 71' and engages a recess 145 formed in section 72'. When the catch hook 144 is not engaged with the recess 145, the trocar adapter 70 can be opened for receiving the trocar 20. After the trocar 20 is received between the sections 71' and 72', the catch hook 144 is engaged with the recess 145 and the trocar adapter 70 is securely closed about the trocar 20 in order to prevent longitudinal movement of the trocar relative to the trocar adapter 70. As clearly understood, the catch hook 144 can extend from either section 71' or 72' and the recess can be formed in the other of the sections 71' or 72'.

Figure 11E:
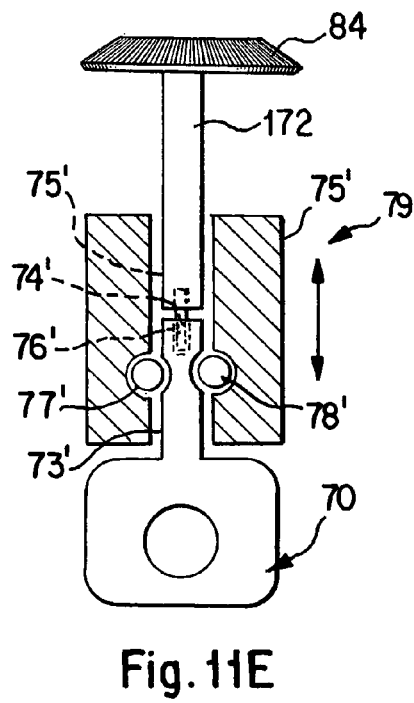
Figure 11C:
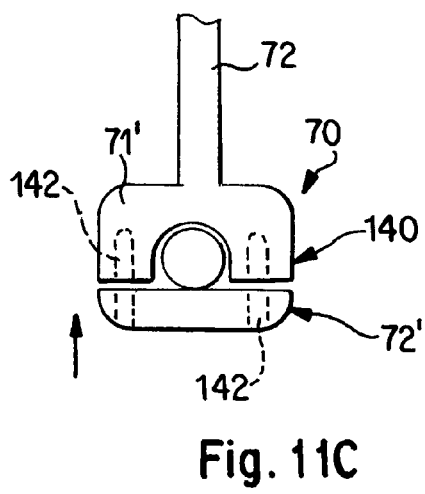

FIG. 11C illustrates another embodiment of the clamping mechanism 140 that includes a first section 71' of the trocar adapter 70 secured to the adapter shaft 72 and a removable cap section 72' that can be separated from the first section 71' in order to introduce the trocar 20 into the trocar adapter 70. After the trocar 20 has been introduced, the cap section 72' can be secured to the first section 71' by threaded or push-in fasteners 142, such as those discussed above with respect to FIG. 11A.

FIG. 11D illustrates an embodiment in which the clamping mechanism 140 includes two pivotable sections 71' or 72' that are spring biased toward each other by a spring 146. Any known type of spring can be used for spring 146, for example a helical coil spring is shown in FIG. 11D. As can be understood, the spring 146 biases the sections 71' or 72' toward each other in order to keep the trocar adapter 70 closed about the trocar 20. However, when the trocar 20 is to be removed or inserted, handles 147 are grasped and squeezed toward each other and opposite to the bias of spring 146. This action opens the trocar adapter 70. When the trocar 20 has been inserted/removed from the trocar adapter 70, the handles 147 are released and the spring 146 forces the sections 71' or 72' toward each other in order to securely hold the trocar 20 within the trocar adapter 70.

Figure 11F:
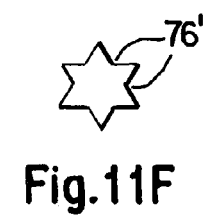

FIG. 11E illustrates an embodiment in which any one of the above-discussed embodiments of the trocar adapter 70 includes a coupling system 79' with a shaft 73' that is removably and rotationally secured to an adapter shaft 172 for easy removal of the trocar adapter 70. The adapter shaft 172 is substantially the same as shaft 72 except for that discussed below. The shaft 73' includes a recess 74' that receives a multi-sided member 75' extending from an end of the adapter shaft 172 as illustrated in FIG. 11F. The member 75' has a plurality of flat, elongated surfaces 76' that engage corresponding surfaces of the recess 74' in order to transfer rotational motion of the shaft 172 to the shaft 73'. The connection between the shaft 73' and the shaft 172 illustrated in FIG. 11E is enclosed by a connector including a movable outer sleeve 75' that has an internal groove 77' for receiving ball bearings 78'. The release of the trocar adapter 70 from the shaft 172 can be accomplished by sliding or otherwise moving the outer sleeve 75' as described in U.S. Pat. No. 5,470,180 to Jore that is hereby incorporated by reference. However, other known quick release couplers, including those discussed above, can also be used. Additionally, the trocar adapter 70 can be easily and quickly removed if a larger or smaller sized trocar adapter 70 is needed during the medical procedure.

In any of the discussed embodiments, the adaptor shaft, including shafts 72, 172 (herein after all identified as "72" for clarity and ease of understanding) is received and supported by bearings 76 (or bushings) in a first end 43 of the middle section 44 or a removable, disposable sleeve 198 that covers an end of the middle section 44. These bearings 76 permit the rotation of the adapter shaft 72 and the laparoscope 12 relative to the middle section 44 in response to the operation of a motor system including a first gear 84, a cooperating second gear 85 and a motor assembly 88. The adapter shaft 72 includes the first gear 84 of a matched set of beveled gears 83. The second gear 85 of the matched set 83 is securely attached to a drive shaft 87 of an X axis motor assembly 88 contained within the middle tubular section 44 of the C-shaped arm 40. As shown in FIG. 2, the gears 84 and 85 mesh with each other so that the first gear 84 and the trocar adapter 70 will rotate when the rotation of the drive shaft 87 causes the second gear 85 to rotate. By running the X axis motor assembly 88 in forward or reverse, the adaptor shaft 72, the adaptor 70, the trocar 20, the laparoscope 12 and the Z-axis laparoscopic drive assembly 60 are rotated about the radial plane of the X axis. This allows the surgeon or attendant to control the position of the laparoscope 12 and the provided image around the X axis in a 180-degree radius as measured from the incision point in the abdomen. The laparoscope 12 will also pivot about the point where it is secured to the adapter 70. As illustrated in FIG. 2, the laparoscope 12 will pivot about the point 490 that is located outside the body of the patient so that the skin of the patient will not be injured during the rotation of the laparoscope 12.

The laparoscope 12 can also be rotated about a "Y" axis so that additional manipulation of the laparoscope's 12 field of view can be achieved. The Y axis rotation of the laparoscope 12 is accomplished by the rotation of the entire C-shaped arm 40 about the Y axis. The Y axis extends perpendicular to the X axis about which the trocar adapter 70 rotates and the direction that the laparoscope moves in response to the rotation of the rollers 63, 64.

Figure 6:
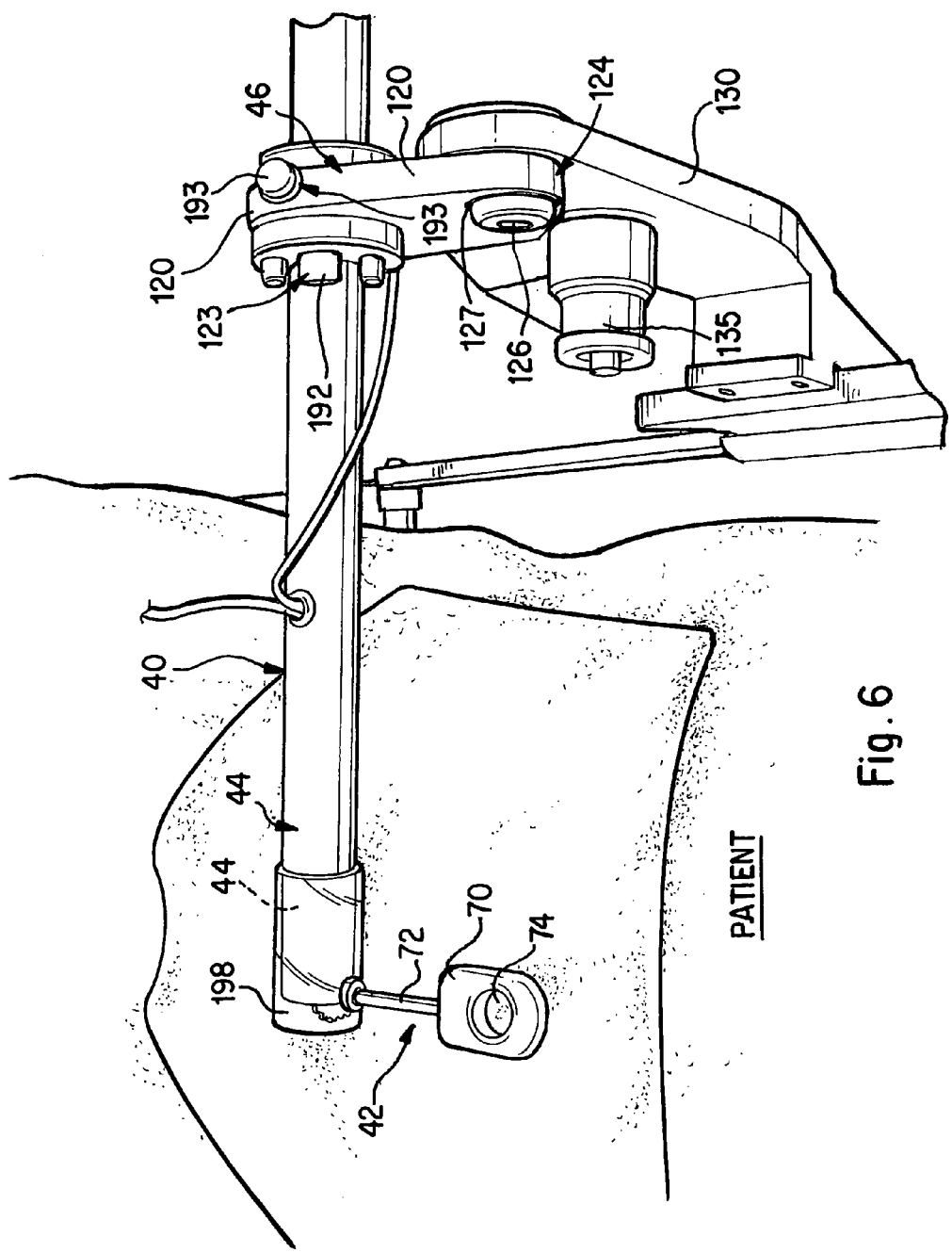
FIG. 6 illustrates the apparatus of FIGS. 1A and 1B before an endoscope is introduced into the trocar adapter.

As shown in FIGS. 1A, 1B, 2 and 6, the second end section 46 of the C-shaped arm 40 includes the fixed link segment 120 that is connected at a first end 122 to the middle section 44 and at a second end 124 to a gearbox assembly 130. The first end 122 of the fixed link 120 includes an internal linear bearing 196 that receives an end of the middle section 44 of the C-shaped arm 40 so that the distance the trocar adapter 70 is spaced from the stanchion 90 can be adjusted. In one embodiment, the linear bearing is a ball bearing. Also, a clamp or other known holding/friction member 123 can be positioned over the end of middle section 44 and the fixed link 120 to prevent their relative movement. For example, as illustrated in FIG. 6, the member 123 includes a piece of friction material 192, such as DELRIN plastic or any other known friction causing material, that is coextensive with at least a portion of the middle section 44 that extends through the fixed link 120. The friction material 192 extends between the linear bearing and shaft of middle section 44. A thumbscrew or knob 193 is connected to a shaft 195 that is threaded into the fixed link 120. When the knob 193 is rotated so that the shaft 195 advances into the fixed link 120, the friction member 123 engages middle section 44 and prevents it from moving relative to the fixed link 120. The middle section 44 can be moved relative to the fixed link 120 by hand, by a motor or by using a motor combined with manual manipulation. The motor can be used for stepwise distance adjustments and the manual manipulation can be used for finite distance adjustments. Alternatively, the end of middle section 44 is secured to the inner surface of an opening 125 in the fixed link 120 in a known manner.

The second end 124 of the fixed link 120 includes fixed shaft 126 that is securely positioned within an opening 127 so that it will not rotate relative to the fixed link 120. Instead, the fixed shaft 126 transfers any imparted rotary motion to the fixed link 120 and the C-shaped arm 40. The fixed shaft 126 is spaced from a center point of the fixed link's length so that eccentric rotational movement of the fixed link 120 can occur. As shown in FIGS. 2 and 6, the fixed shaft 126 is also secured to a first gear 132 located within a gear housing 130. A Y-axis motor system includes the first gear 132, a Y-axis drive gear 134, a drive shaft 136 and a motor 135. As illustrated, the first gear 132 engages the Y-axis drive gear 134 secured to an end of the drive shaft 136 extending from the Y-axis motor 135. The rotation of the drive shaft 136 during the operation of the Y-axis motor 135 causes the meshed first gear 132 to rotate. This in turn causes the fixed link 120 and the other sections 42, 44 of the C-shaped arm 40 to rotate about the Y axis. The Y-axis motor 135 can be located in the housing 92 and the drive shaft 136 can extend through the drive member 91 or form part of the drive member 91. In this embodiment, the gear 134 is positioned within the gearbox housing 130 with gear 132. Alternatively, as shown in FIGS. 1A, 1B and 6, the Y-axis motor 135 is secured directly to the gearbox housing 130 that contains the gears 132 and 134. In the embodiment illustrated in FIGS. 1B and 6, the stanchion 90 is secured directly to gearbox housing 130. Operation of the Y-axis motor 135 either in forward or reverse as controlled by the surgeon or surgeon assistant attains angular displacement of the laparoscope 12 as measured perpendicular from the abdominal wall. A total of about 210 degrees of rotation of the C-shaped arm about the Y axis is possible using the Y-axis motor 135. The actual amount of rotation will be limited by the position of the apparatus 10 to the body of the patient. Typically, the total achieved rotational motion with the patient present can be about 180 degrees. Without the patient and motor 130, the total rotation could be 360 degrees.

A remote actuating control unit 150 for the movement of the C-shaped arm 40 and the laparoscope 12 is comprised of common single or double pole momentary electrical switches 152-156 typical to those skilled in the field. Wiring of the switches 152-156 is typical of electric circuitry used to control DC motor on/off momentary functions. Forward and reverse motor control is accomplished by reversing electrical polarity through the momentary switches 152, 153, respectively, in the control unit 150 as is known. FIGS. 1A and 1B also illustrate the left and right rotational switches 154, 155, respectively, and the longitudinal Z-axis endoscope movement switch 156.

Figure 10:
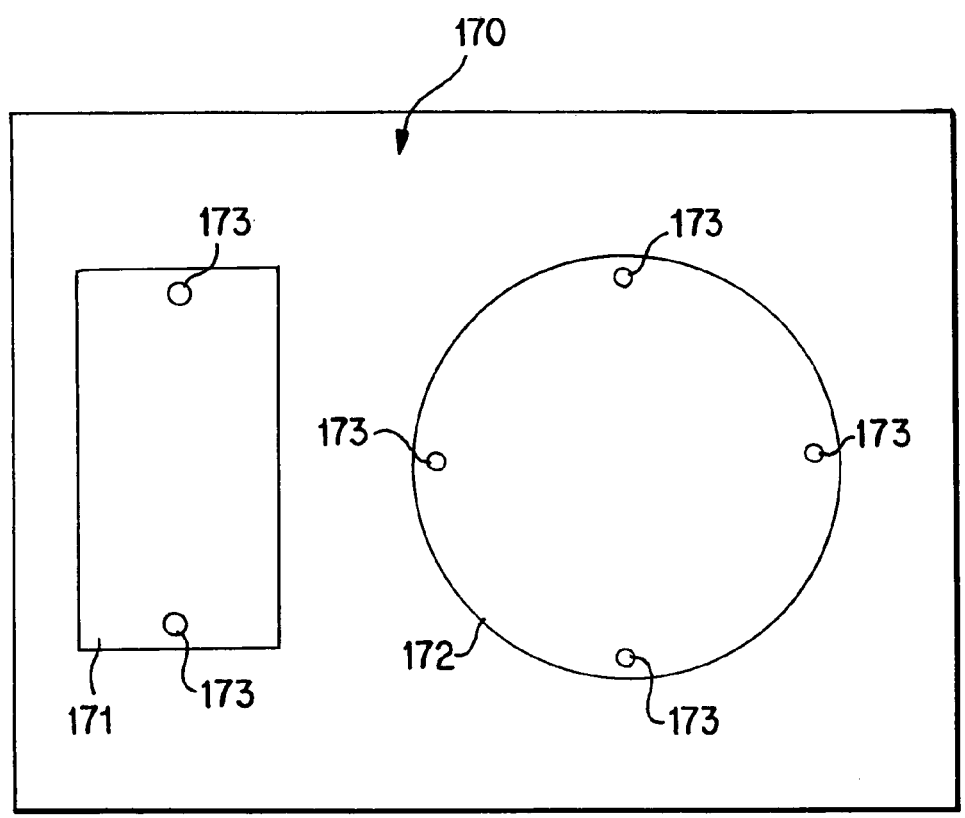
FIG. 10 illustrates a foot-activated controller that can be used with the apparatus shown in FIGS. 1A and 1B.

In addition to the control unit 150, the movement of the C-shaped arm 40 and laparoscope 12 can also be controlled using a remote actuator in the form of a foot activated controller 170 illustrated in FIG. 10. In one embodiment, the foot activated controller 170 includes at least one foot pedal. In a preferred embodiment, the foot activated controller 170 includes a plurality of foot pedals 171, 172 as described in U.S. Pat. No. 5,907,664 to Wang et al., which is fully incorporated herein by reference. In one embodiment, the foot activated controller includes the first and second foot pedals as disclosed in U.S. Pat. No. 5,907,664. In this embodiment, the foot pedal 172 has a plurality of spaced pressure transducers or switches 173 that can be simultaneously activated to achieve movement of the C-shaped arm 40 and the laparoscope 12 in multiple directions at the same time (complex motion). For example, the first foot pedal can be used to control the translational movement of the laparoscope 12 into and out of the body. The second pedal 172 can be used to control the separate or simultaneous rotational motion of the trocar adapter 70 and the C-shaped arm 40.

Alternatively, in another embodiment, the foot activated controller includes three toggled pedals. Each toggled pedal is able to contact one of two associated motion direction switches. When a pedal is toggled in a given direction (forward or backward; left or right) an associated switch is closed and the C-shaped arm 40 and the laparoscope 12 move in a predetermined path of motion that is assigned to the closed switch. In this embodiment, one of these toggled pedals controls the direction of the rotational movement of the trocar adapter 70. The second of the pedals controls the rotation of the C-shaped arm 40, while the third pedal controls the translational movement of the laparoscope 12 into and out of the body.

In any of the above embodiments, the foot activated controller 170 is wired in parallel with the control unit 150 so that the surgeon or operator of the C-shaped arm 40 has the option of controlling the movement of the C-shaped arm 40 and the laparoscope 12 with the hand-activated control unit 150 or the foot-activated control unit 170. Alternatively, the control unit 150 and the foot activated controller can be separately wired.

In yet another embodiment, a control unit for the positioning of the C-shaped arm 40 and the laparoscope 12 could include voice recognition software and a computer having a processor that causes one or more motion control switches to be activated when the software identifies a directional command given by an attendant or the surgeon. The motion control switches will cause the C-shaped arm 40 and the laparoscope 12 to move according to the voice commands.

Electric cables and connectors used to carry voltage and amperage for motor control unit 150 are typical of components used in the low voltage direct current electric industry. Of course wireless remote control technology can also be used to control the "X","Y" and "Z" axis drive motors. The wireless control could be similar to the key ring control for automobile alarm systems, which typically control solenoids that unlock and lock your car doors and open the trunk. Such a system utilizes switches in the remote control unit that reverse polarity in a solenoid to actuate the lock mechanism either open or closed.

Figure 18:
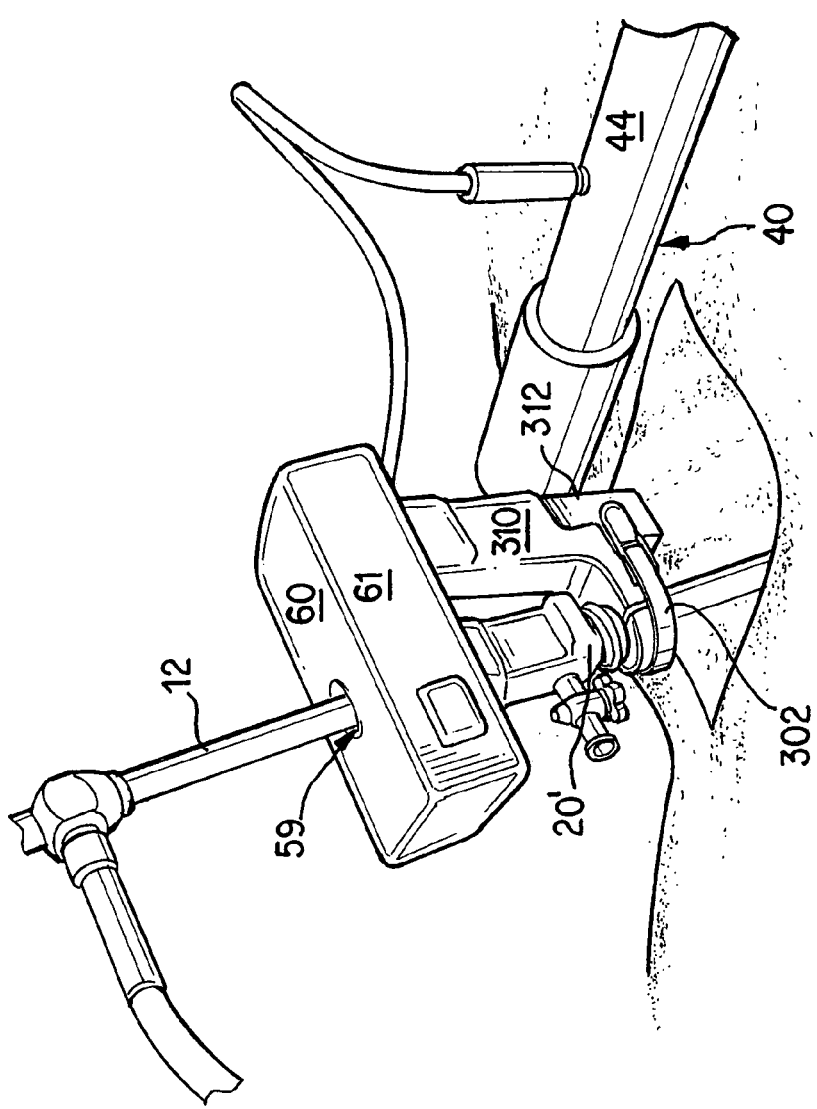
FIGS. 18 and 19 illustrate an alternative embodiment of a trocar support member according to the present invention.

As illustrated, the present invention includes additional alternative embodiments for moving the medical instrument 12 along the Z axis. In an alternative embodiment shown in FIG. 18, the trocar 20' is releasably secured to an adapter 310 that carries and supports the housing 61 for the endoscopic instrument drive assembly 60. In this embodiment, the trocar 20' is held within a releasable clamp 302 that includes a pivotable clamping member 304 with a first end 305 that pivots relative to the support adapter 310 and a second end 306 that is releasably held by a locking protrusion 307. In this embodiment, the support adapter 310 can be permanently or releasably secured to the first end section 42. For example, the support adapter 310 can include a post 312 that extends in the direction of the first end section 42 and that is releasably connected to a portion of the first end section 42 by a quick release coupling, such as a bayonet mount connector, the connector illustrated in FIG. 11E or the connector illustrated in FIG. 24. As seen in the figures, the support adapter 310 can provide an offset jog for the trocar 20' relative to the body of the patient to overcome elevations in the profile of the patient's body. The support adapter 310 also includes a plate 318 that can support the lower surface of the housing 61 or that can form the lower surface of housing 61. The housing 61 can include any of the motor and roller arrangements disclosed herein for moving either the endoscopic instrument 12 or the trocar 20'.

Figure 19:
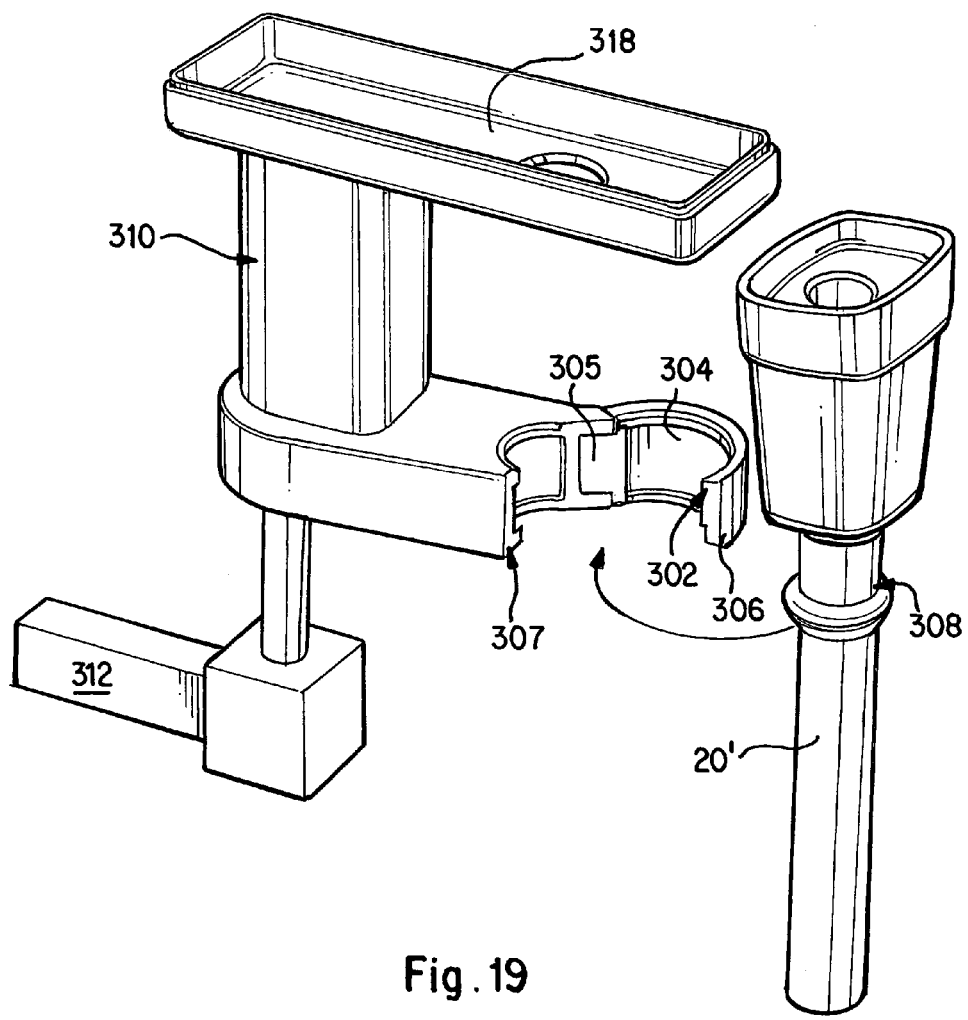

As shown in FIG. 19, the trocar 20' in this embodiment can include a necked region 308 for receiving the clamping member 304. Additionally, the area above the necked region 308 can have any configuration that permits trocar 20' to mate with the plate 318 and be aligned with the instrument receiving opening 59 within the housing 61 and receive the instrument 12 as it moves along the Z axis.

Figure 20:
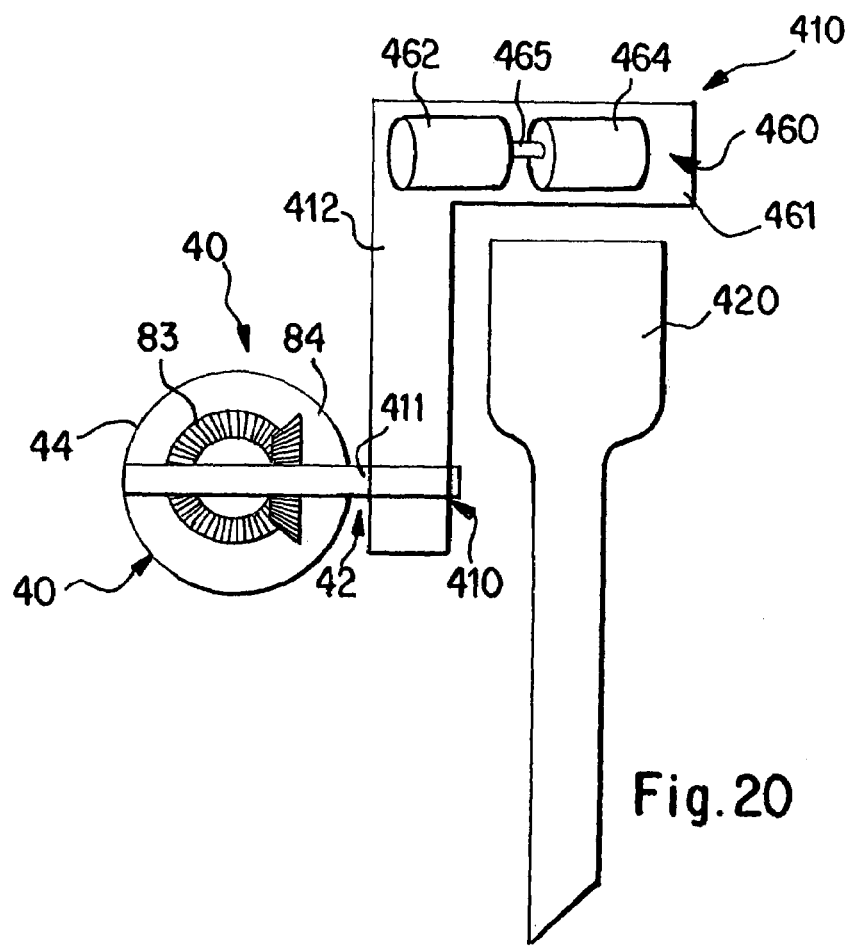
FIG. 20 is a schematic view of a support member for a medical instrument that is free of an attachment to a trocar according to another embodiment of the present invention.
Figure 22B:
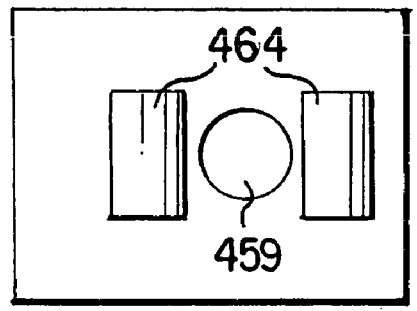
FIGS. 22A and 22B are schematic views of the support member of FIG. 20 with drive rollers in alternative alignments, perpendicular to that shown in FIG. 20.
Figure 22A:
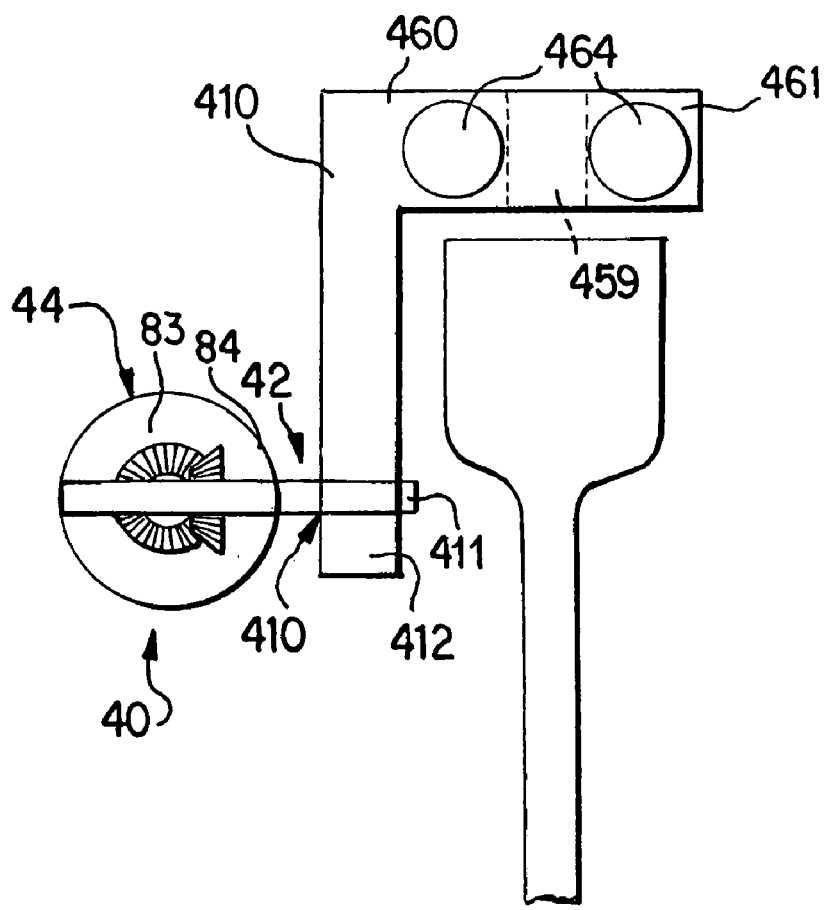

In the embodiment illustrated in FIG. 20, the first end section 42 is connected to a support adapter 410 by any connection discussed herein, for example a quick release coupling such as those discussed herein. The first end section 42 is capable of rotating relative to section 44 as discussed above. Additionally, like the other support adapters discussed herein, support adapter 410 can include a height adjustment mechanism, discussed below, that allows the distance between the body of the patient and a motor drive assembly 460. The support adapter 410 includes a first elongated shaft 411 that can be releasably coupled to the first end section 42 and a vertical member 412 connected to the drive assembly 460 that includes a housing 461 carrying rollers for driving the endoscopic instrument 12. The drive assembly 460 is similar to drive assembly 60 except for the points discussed below. The support adapter 410 does not include a connection to the trocar 420. Instead, the trocar 420 is able to move independent of the support adapter 410 prior to the insertion of the endoscopic instrument 12 into both the motor housing 460 and the trocar 420. The trocar 420 is held within the body by the friction between the skin at the surgical opening and the outer surface of the trocar 420. This friction is greater than the friction between the trocar 420 and the received endoscopic instrument 12. As understood, when the endoscopic instrument 12 is positioned within the trocar 420, the trocar 420 will rotate with the rotation of the endoscopic instrument in response to the motion of the support adapter 410 and the first end section 42.

Figure 21:
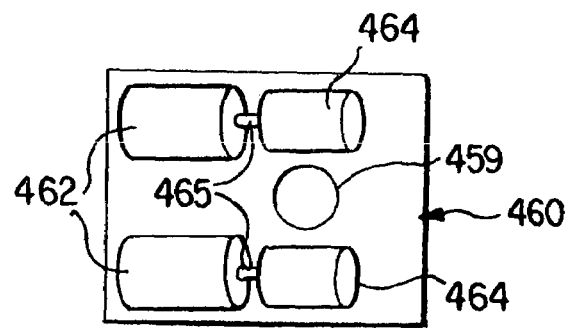
FIG. 21 is a schematic top view of the support member of FIG. 20.

The drive assembly 460 includes an opening 459 for receiving the endosopic instrument 12 and through which the endoscopic instrument 12 moves as it is advanced or retracted along the Z axis. As shown in FIGS. 20 and 21, the drive assembly 460 includes a pair of drive motors 462 and a pair of associated drive rollers 464 that are connected to the output shafts 465 of the motors 462. A friction material, as discussed above with respect to roller 63, 64, for engaging and driving the endoscopic instrument 12 along the Z-axis, covers each roller 464. The motors 462 and rollers 464 can be moveable within the housing 461, for example on moveable chassis, and lockable in multiple positions in order to adjust the space between the rollers 464. As a result, endoscopic instruments 12 of different sizes (diameters) can be accommodated between the rollers 464 and driven without slippage. In an alternative embodiment, the drive assembly 460 can contain a single driven roller 464 and an idler roller as discussed above.

An embodiment of a quick release coupling between two parts of an adapter 410' is illustrated in FIGS. 38A-38J. In this embodiment, a portion 413' of the adapter 410' is connected to the first end section 42. This portion 413' includes a plurality of flat surfaces 411', a recessed groove 412' and movement limiting plates 414'. The end of a cooperating vertical support member 417' includes a jaw 415' that cooperates with, and clamps around, the portion 413' of the adapter 410' between the movement limiting plates 414'. A sliding member 415' moves at the end of the adapter 410' from a first, open position at which the jaw is open to receive the portion 413' to a second, closed position where the sliding member 415' moves along the groove 412' and beneath the portion 413' to hold the vertical portion 417' of the adapter 410' on the first end section 42. As illustrated, the adapter 410' includes a plurality of through holes 420' that are spaced from each other along the length of the member 417'. In this embodiment, a drive assembly 820' has a housing 821' that includes a spring loaded pin, rod or threaded member 830' that can be removably positioned within one of the through holes 420' corresponding to a desired height of the trocar 20 relative to the body of the patient. The drive assembly 820', such as any of those disclosed herein, can include an opening 822' in its housing 821' for receiving the adapter 410' so that the drive assembly 820' can adjustably move along the length of the adapter 410'.

In the embodiment illustrated in FIGS. 38A-38J, the drive assembly 820' is substantially identical to motor drive assembly 820 illustrated in FIGS. 34-37. Like elements of these embodiments are identified using the same reference numerals. In addition to opening 822', the drive assembly 820' also includes a cage 851' that maintains the rollers 834, 835 in alignment with each other. In a first embodiment, these rollers 834, 835 are aligned in parallel with each other. Also, the pivotable first housing section 842' includes a lever 843' that is pivotably secured to the cage 851' about a point 845' for holding the pinch roller 834 in position and moving the pinch roller 834 relative to the drive roller 835.

Figure 38A:
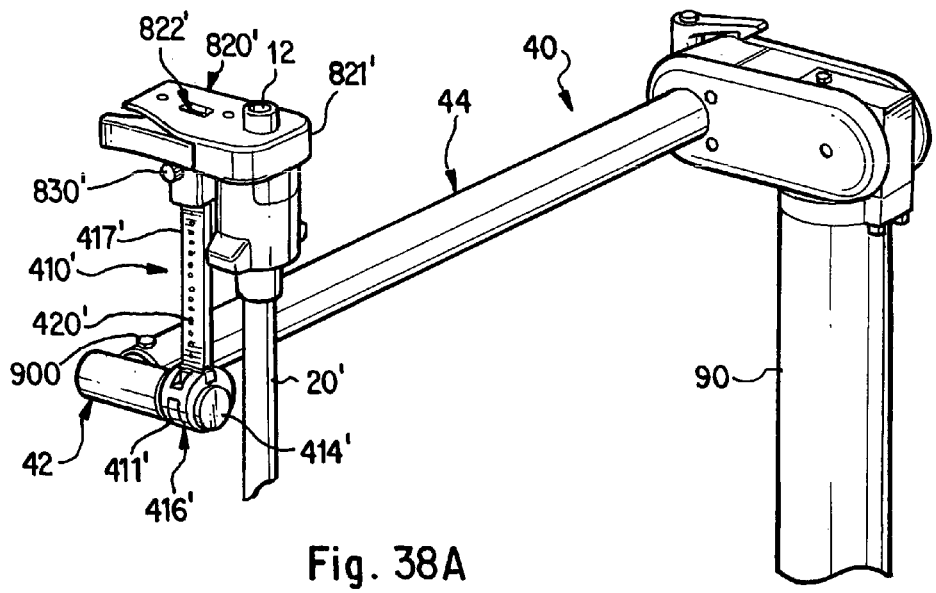
FIGS. 38A-38E illustrate an alternative embodiment of an adjustable trocar support member according to the present invention.
Figure 38B:
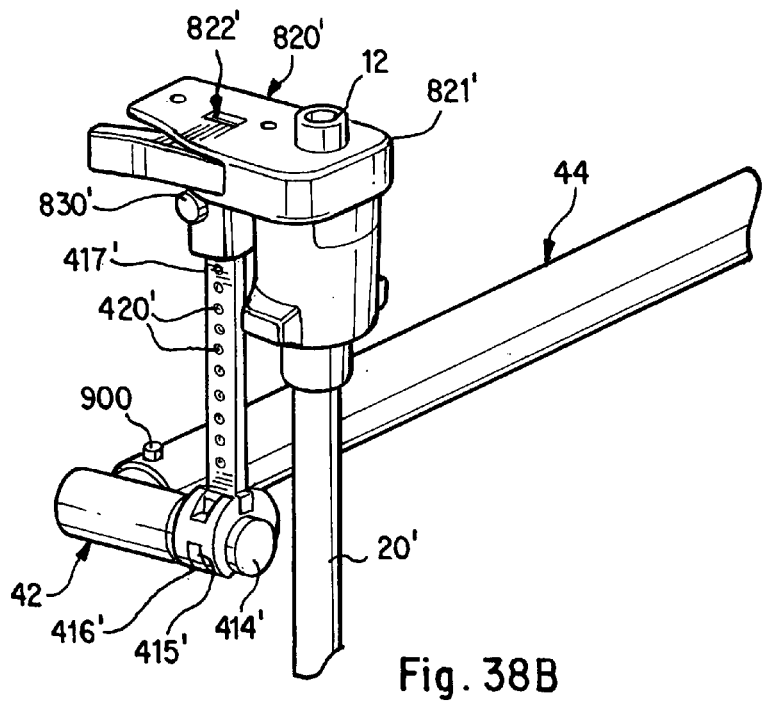
Figure 38C:
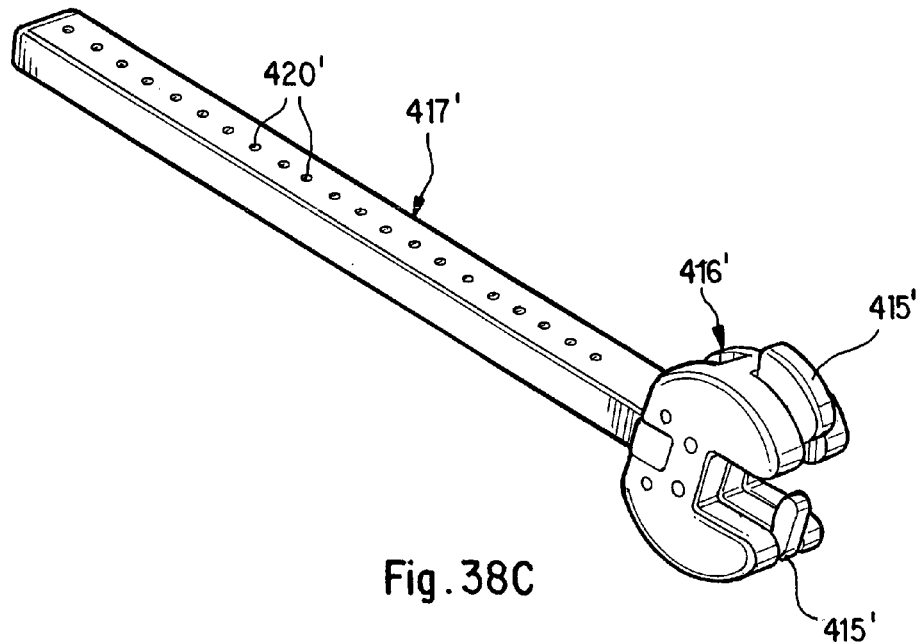
Figure 38D:
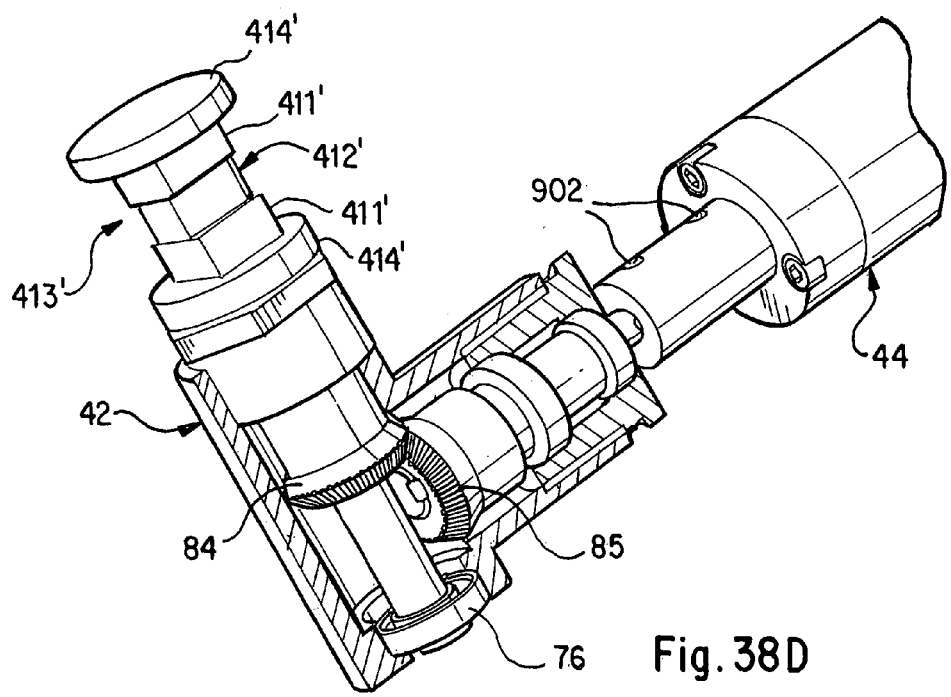
Figure 38E:
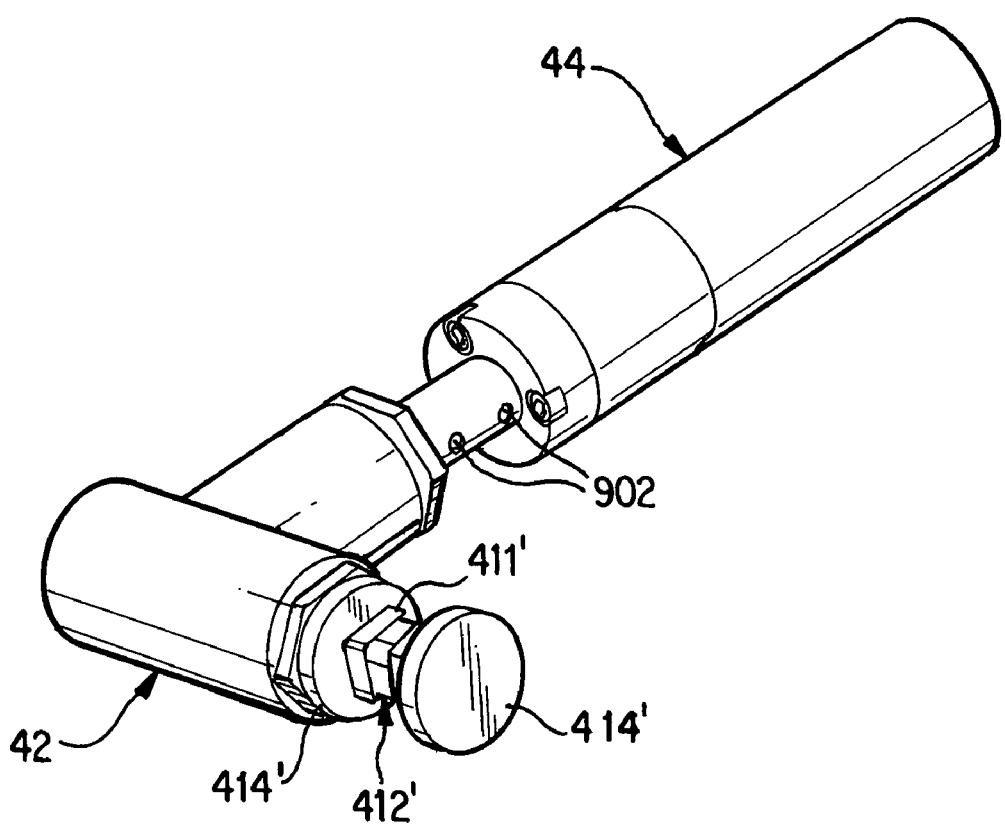
Figure 38F:
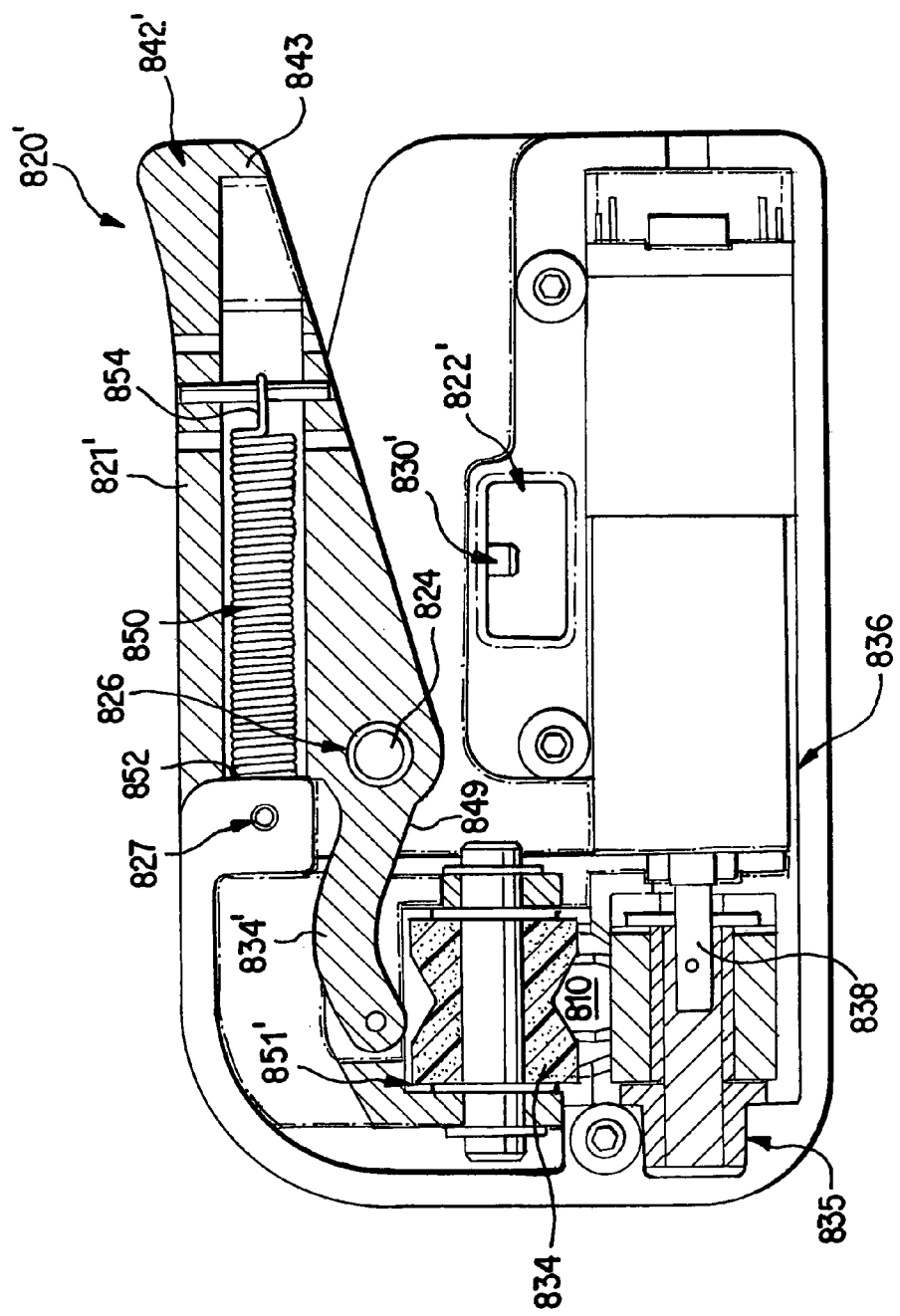
FIGS. 38F and 38G are cross sections of the drive assembly with a pivotable lever in a released position and a depressed position illustrated in FIG. 38A.
Figure 38G:
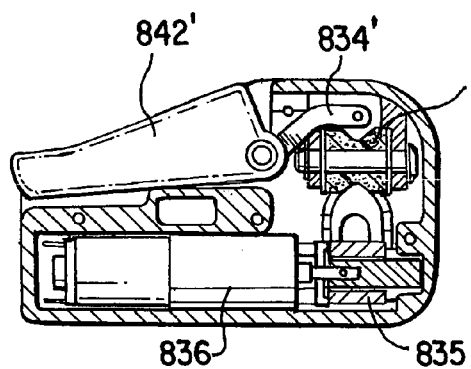
Figure 38H:
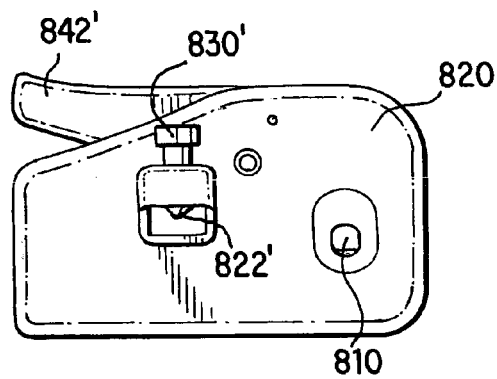
FIG. 38H is a bottom view of the drive assembly illustrated in FIG. 38A.
Figure 38I:
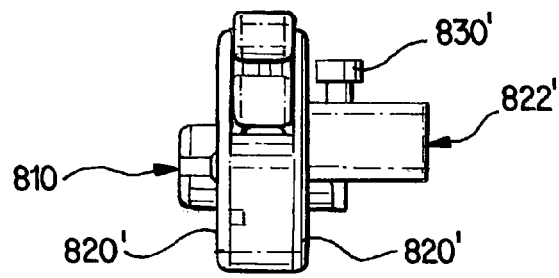
FIGS. 38I and 38J are side views of the drive assembly illustrated in FIG. 38A.
Figure 38J:
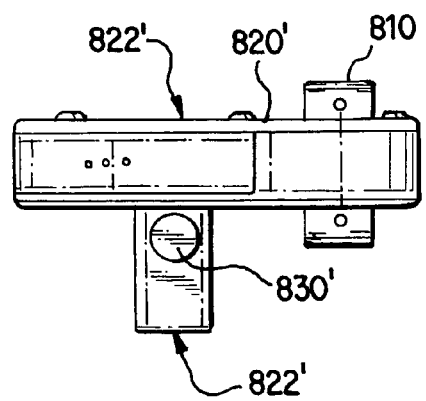

The adapter 410' can be secured to the trocar 20' as shown in FIG. 19 or it can be snap fit or otherwise secured to the housing 821' in accordance with any of the discussed embodiments. FIGS. 38A and 38E also illustrate middle section 44 including a spring loaded pin, rod or threaded member 900 and holes 902 that allows the section 42 to be incrementally and telescopically spaced from the end of the middle section 44.

Figure 23:
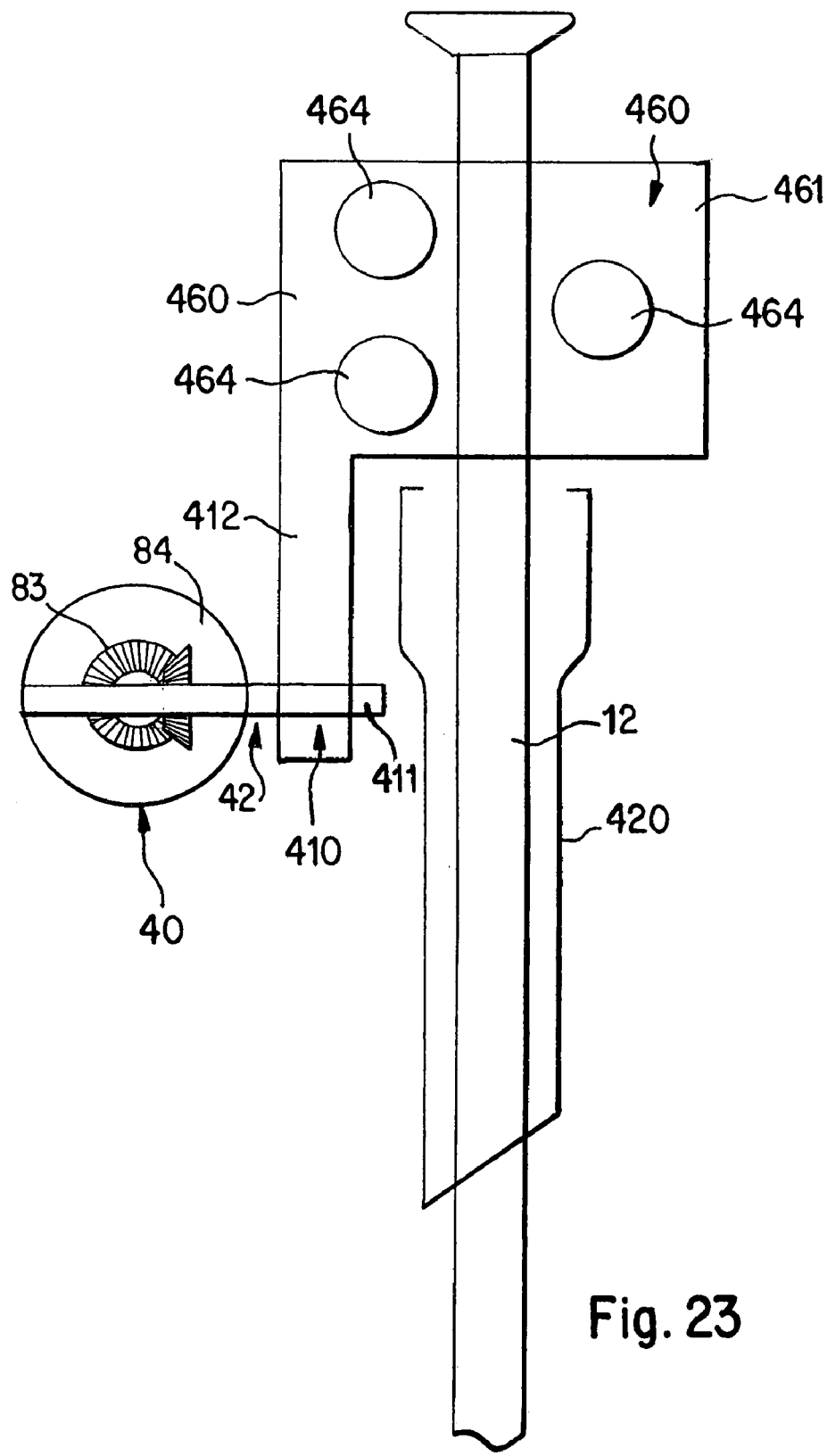
FIG. 23 is a schematic view of the support member of FIG. 20 with an additional roller on one side for supporting the alignment of the medical instrument.

In another alternative embodiment as illustrated in FIG. 23, the drive assembly 460 can include an odd number of rollers 464 (one driven and two idler/two driven and one idler) with a majority of the rollers on one side of the introduced endoscopic instrument 12 in order to orient the endoscopic instrument 12 and maintain its plane relative to the body of the patient. Other motor and roller arrangements discussed herein could also be used within housing 461. For example, the motors could be positioned within the rollers as discussed below.

Figure 24:
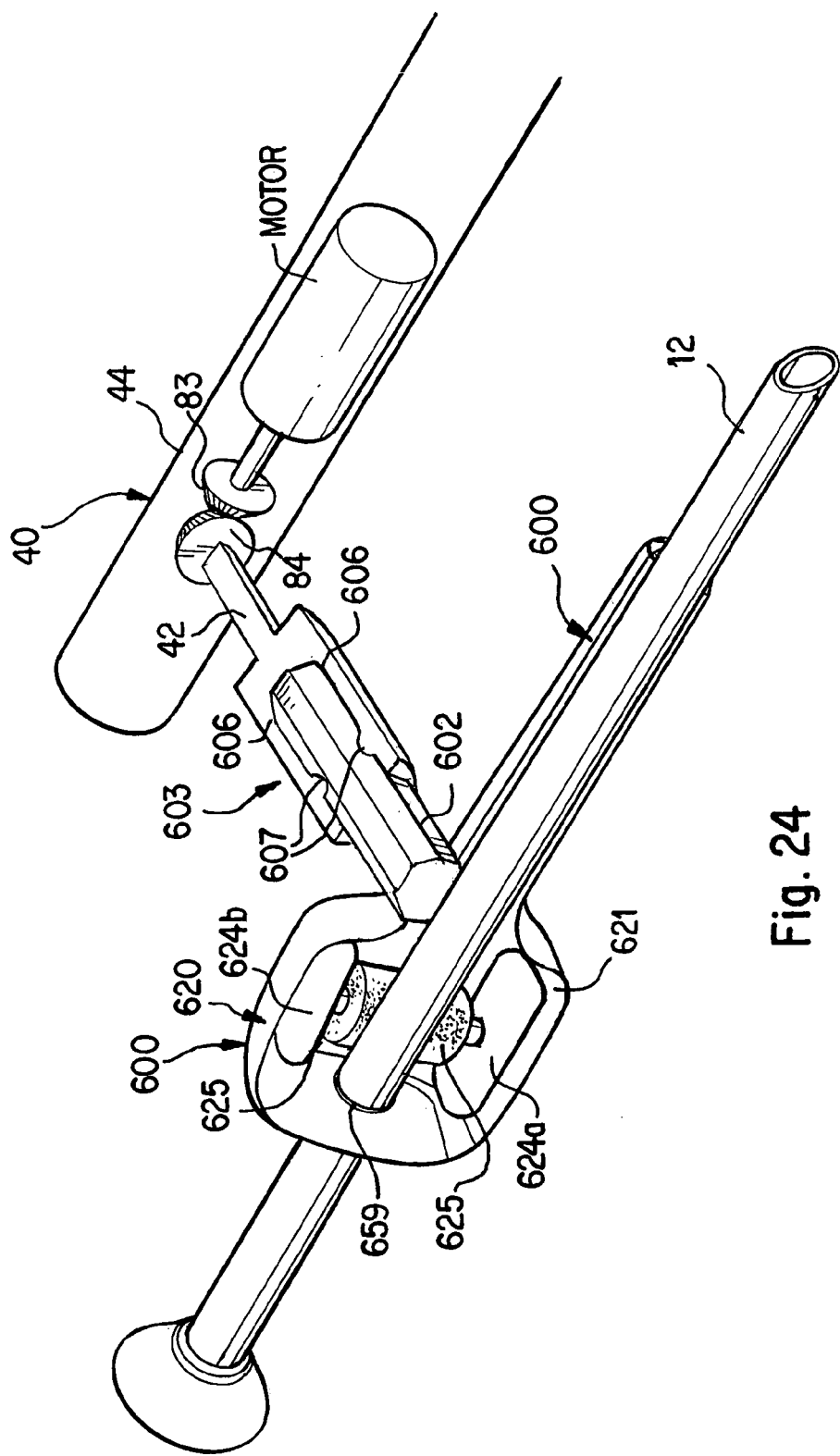
FIG. 24 is a schematic view of a trocar connected to a C-shaped arm according to another embodiment of the present invention, the trocar includes a motor housing with motors and rollers for advancing and retracting a medical instrument.

In another embodiment for moving the endoscopic instrument along the Z axis illustrated in FIGS. 24-30, the present invention includes a trocar 600 with a drive assembly 620 including a drive motor assembly housing 621 that contains at least one drive roller for engaging and moving an inserted endoscopic instrument 12. The trocar 600 can be connected to the first end section 42 by any of the connections, including the quick release couplings discussed herein. For example, as shown in FIG. 24, the trocar 600, in addition to its conventional insulfation valves, can comprise a quick release coupling 603 including a keyed or splined adapter shaft 602 that releasably engages a complimentary receptacle 606 on the end of the first end section 42. Detents 607 can be included in the receptacle 606 for securely holding the shaft 602.

Figure 25:
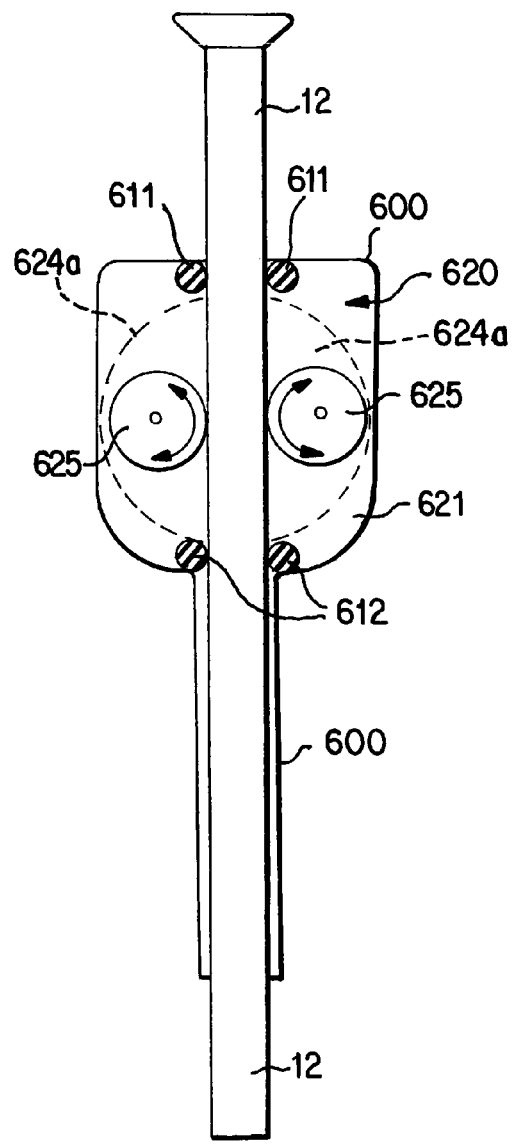
FIGS. 25 and 26 are side schematic views of the trocar of FIG. 24.
Figure 26:
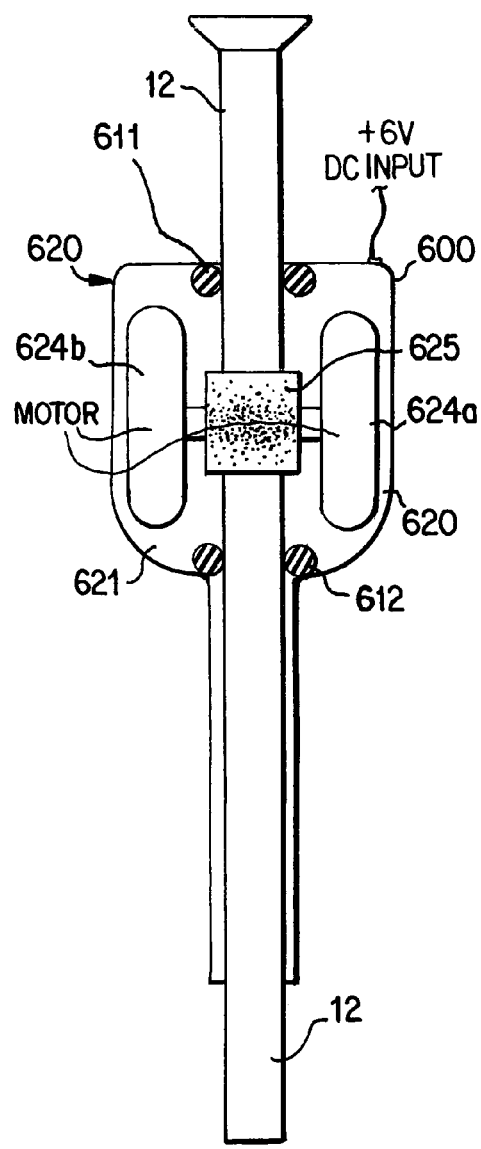
Figure 27:
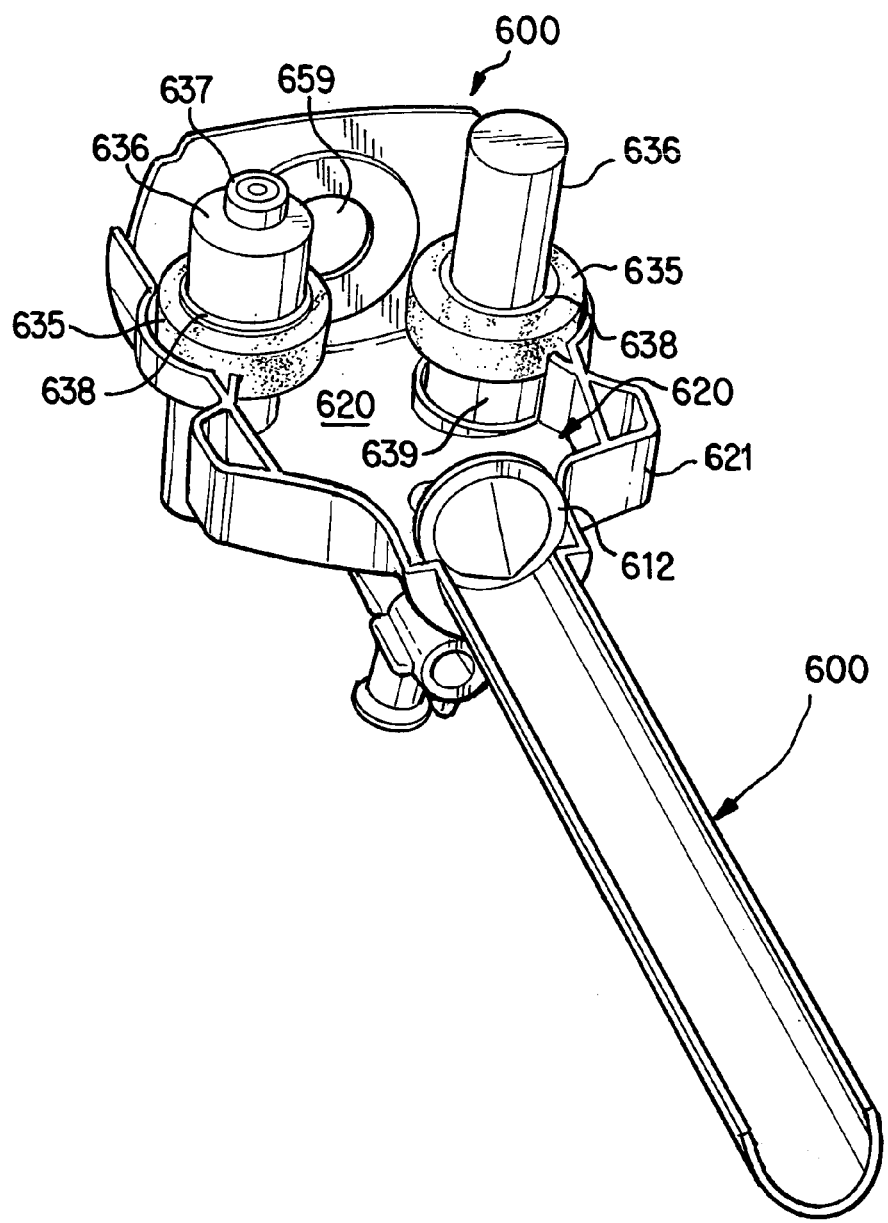
FIG. 27 is a fragmentary view of an embodiment of the trocar with a motor housing having driven rollers carrying centrally positioned motors.
Figure 30:
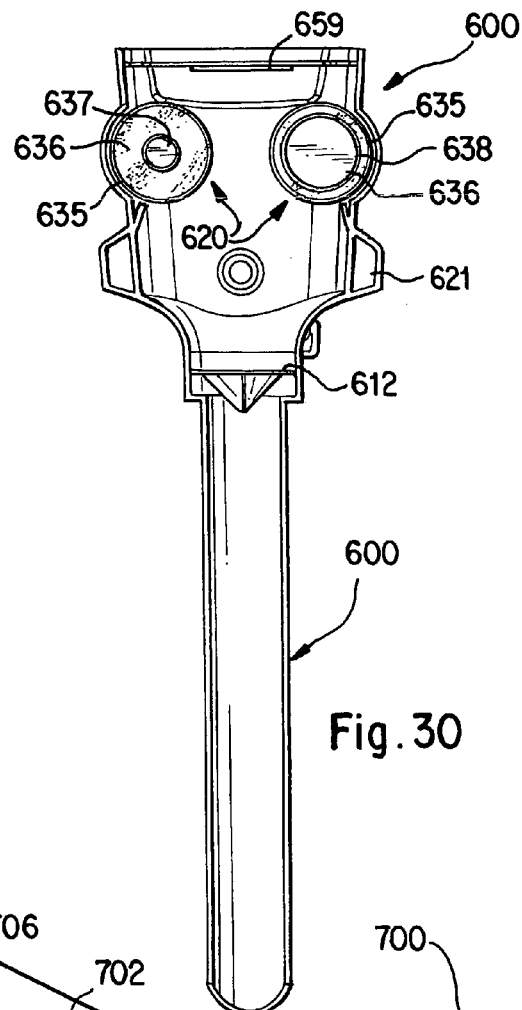
FIG. 30 is a schematic view of the trocar with motor housing of FIG. 27.

As shown in FIGS. 25-27, the trocar 600 also includes a first trocar seal 610 with a seal wiper 611 at an upper opening 659 through which the endoscopic instrument 12 is inserted and a second trocar seal 612, such as a duck bill or flapper valve, at the position where the endoscopic instrument 12 exits the motor housing 621 or just below this position.

The drive assembly 620 can include any combination of motors, drive roller and/or idler rollers. For example, in a preferred embodiment illustrated in FIGS. 24-26, the drive assembly 620 includes a pair of thin profile (pancake) motors 624 (a) and 624(b) that each rotate two rollers 625 in opposite directions for advancing and withdrawing the endocsopic instrument 12 from within the trocar 600.

In an alternative embodiment illustrated in FIGS. 27-30, the drive assembly 620 can include a motor, at least a pinch roller (not shown) and a driven roller 635 or a pair of cooperating driven rollers 635. In a preferred embodiment, the motors 636 for the driven rollers 635 can be positioned within a centrally located opening in the rollers 635 to reduce the size of the motor housing 621. In this embodiment, the each motor 636 extends in a direction opposite that of the other motor 636 within the housing 621. Additionally, each motor 636 includes a drive wheel at one end that engages a support ring 638 on which the associated roller 635 is mounted. The other end of each motor 637 is positioned within a bearing 639 in the housing 620. As a result, when the motors 636 operate, the drive wheels (not shown) engage the support rings 638 secured to the rollers 635 and drive the rollers 635 in their intended direction in order to effect the desired movement (introduction/retraction) of the instrument 12 within the body of the patient. The drive rollers 635 can be formed of a rubber as discussed above and they can be moveable along with their motors 636 within the housing 621 to accommodate instruments 12 having different diameters.

Figure 31:
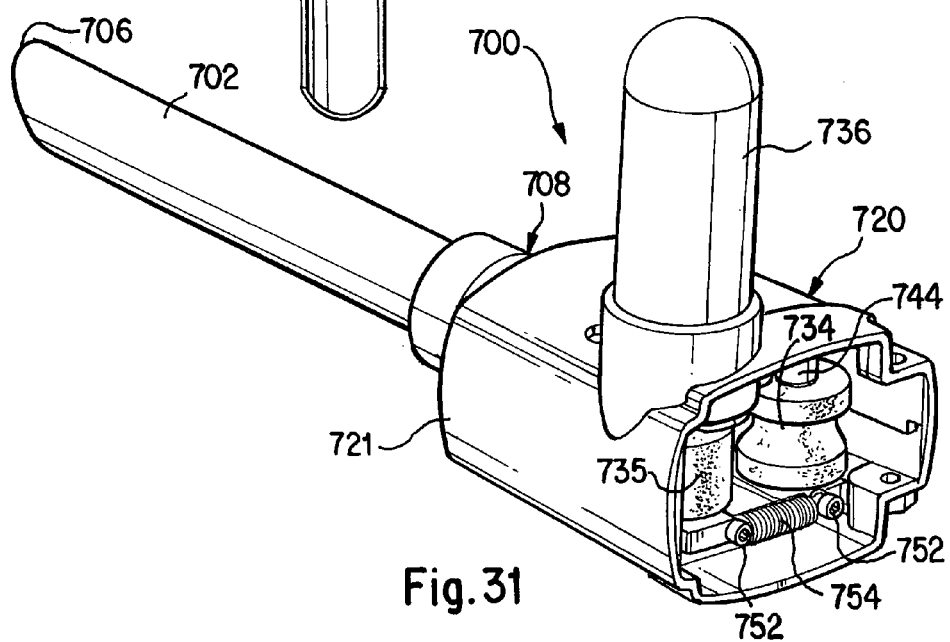
FIG. 31 is an isometric view of a trocar with a trocar motor housing according to an alternative embodiment of the present invention.
Figure 32:
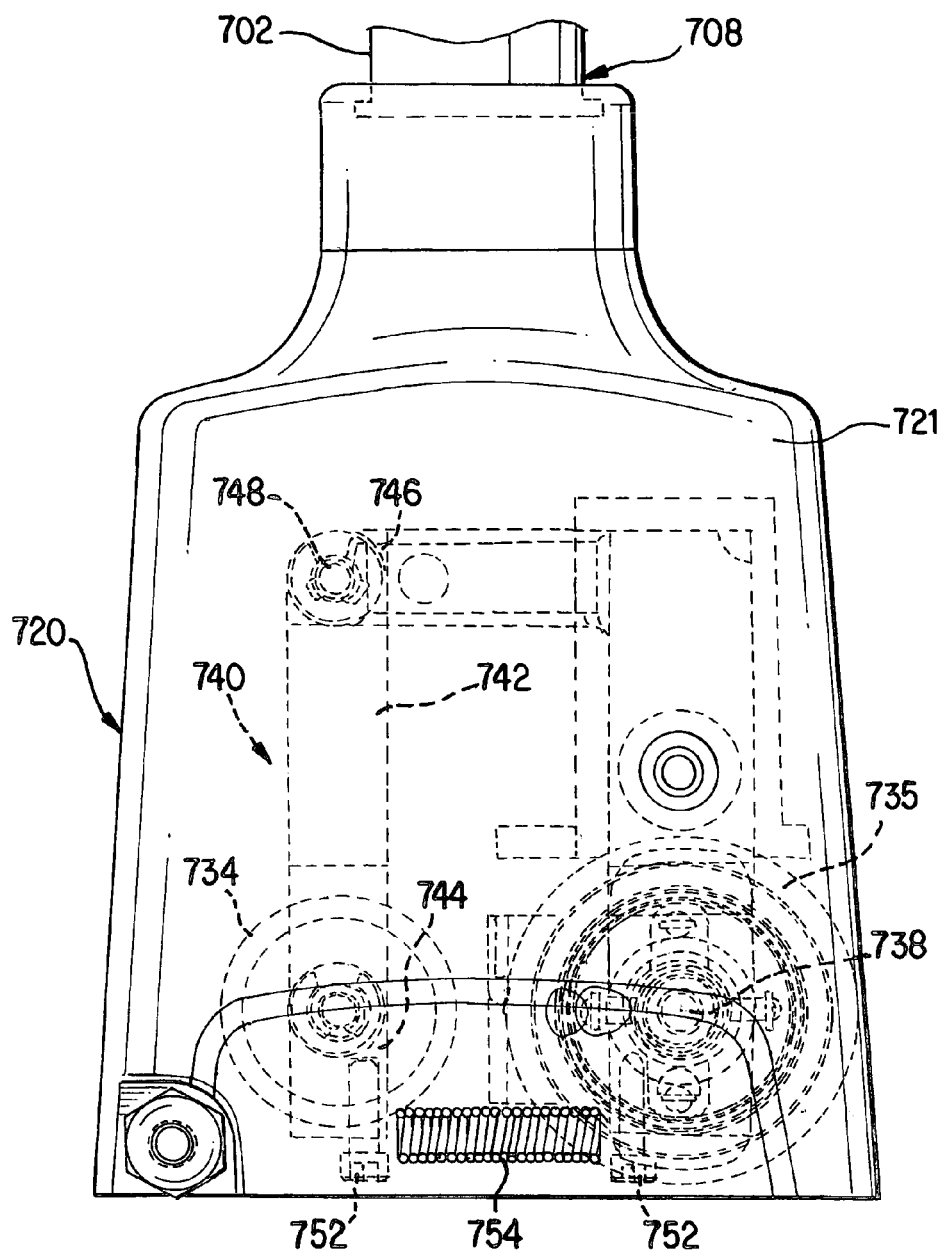
FIG. 32 is a schematic view of the trocar motor housing of FIG. 31 with the internal parts of the trocar motor housing shown in broken lines.
Figure 33:
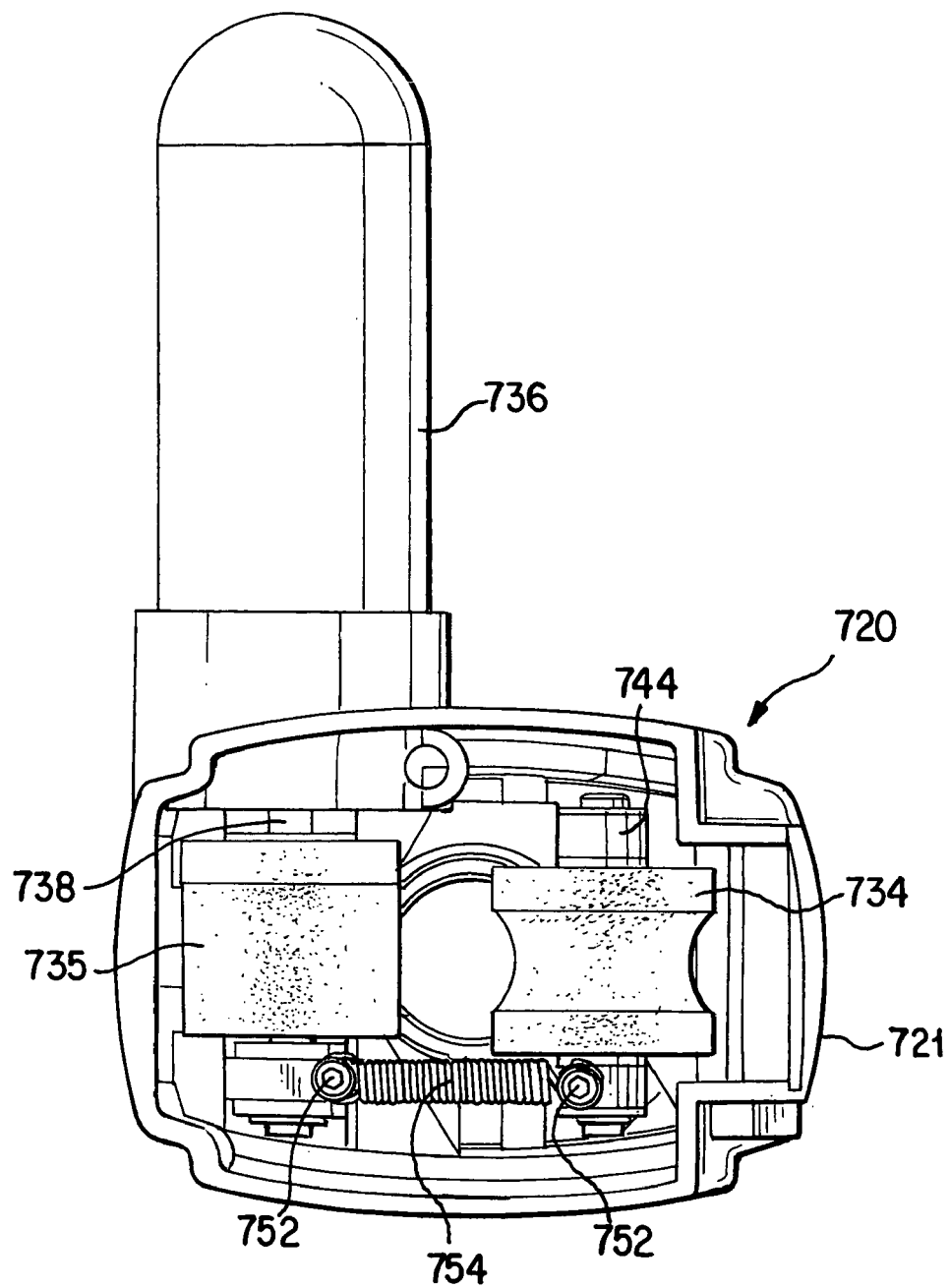
FIG. 33 is a rear schematic view of the trocar motor housing of FIG. 31.

FIGS. 31-33 illustrate an alternative embodiment of the trocar 600. FIGS. 31-33 illustrate a trocar 700 through which an endoscopic instrument 12 can be advanced into, and retracted from, the body of a patient. Like the above-discussed embodiments, the trocar 700 comprises an elongated tubular member 702 having a first, percutaneous or atraumatic tip end 706 and a second, opposite end 708 with to a motor/drive assembly 720 that can be connected to the C-shaped arm 40. The motor/drive assembly 720 includes a housing 721, a driven roller 735 and a pinch (idler) roller 734 that is biased toward the driven roller 735 for contacting the inserted endoscopic instrument 12 in order to advance and retract the endoscopic instrument 12 within the trocar 700. The trocar 700 also includes a motor enclosure 736 that covers a conventional rotary drive motor. In one exemplary embodiment, the drive motor within the enclosure 736 includes a MD 1622 gear motor mated with a MD 15P gear head, both of which are available from Micro-Drives of Clearwater, Fla.

As understood, the drive motor includes an output shaft 738 connected to the driven roller 735 for transferring the rotational movement of the output shaft 738 to the driven roller 735. As a result, the driven roller 735 will rotate in response to the rotation of the output shaft 738 and in the direction dictated by the rotational direction of the output shaft 738. Therefore, when the output shaft 738 rotates in a first direction, the driven roller 735 will rotate in a direction that advances the endoscopic instrument 12 into the body of the patient. Conversely, when the output shaft 738 rotates in a second, opposite direction, the driven roller 735 will rotate to retract the endoscopic instrument 12 from within the body of the patient.

As illustrated in FIGS. 32 and 33, the pinch roller 734 is biased toward the driven roller 735 by a biasing mechanism 740. In a first embodiment illustrated in FIG. 32, the biasing mechanism 740 includes a pivotable arm 742 having a first end 744 securely connected to the pinch roller 734 and a second, opposite end 746 securely connected to a pivot point 748 located within the housing 721 so that the pivotable arm 742 and pinch roller 734 can rotate relative to the driven roller 735 about the pivot point 748. Elongated member 752, such as rigid pins, extends from the support shafts for both the pinch roller 734 and the driven roller 735. A spring 754 is attached to each elongated member 752 and extends between these elongated members 752 as shown in FIGS. 31-33. The spring assumes an extended state when an endoscopic instrument is positioned within the trocar 700. The tension force of the spring 754 causes relative motion between the pinch roller 734 and the driven roller 735 so that an endoscopic instrument 12 that extends through the housing 721 is pinched between the pinch roller 734 and the driven roller 735. As a result, the rotation of the rollers 734, 735 causes the endoscopic instrument to move within the trocar 700.

The spring 754 can be changed so that the pinching force applied to the endoscopic instrument by the rollers 734, 735 can be adjusted. For example, when the pinching force applied by the rollers 734, 735 needs to be reduced, a longer spring or a spring with a smaller spring coefficient can be connected to each elongated member 752 and between the rollers 734, 735. In an alternative embodiment, both ends 744, 746 of the elongated arm 742 could be linearly moveable relative to the driven roller 735. In this alternative embodiment, a spring 754 could be positioned at both ends of the arm 742 and connected to one or more pinch rollers for forcing the roller(s) into engagement with an inserted endoscopic instrument and toward the driven roller 735. This is advantageous when the motor/drive housing 720 includes a plurality of pinch rollers 734 and a plurality of driven rollers 735. This is also advantageous when a driven roller 735 is positioned between two spaced pinch rollers 734.

FIGS. 34-37 illustrate an alternative embodiment of an apparatus for driving a medical instrument relative to a patient according to the present invention. The apparatus includes drive assembly 820 including a motor housing 821. Like the other embodiments discussed above, openings 810 in the drive assembly housing 821 are axially aligned with a passageway that extends between a pinch roller 834 and a driven roller 835 for receiving an endoscopic tool 12 (see FIG. 35).

Figure 34:
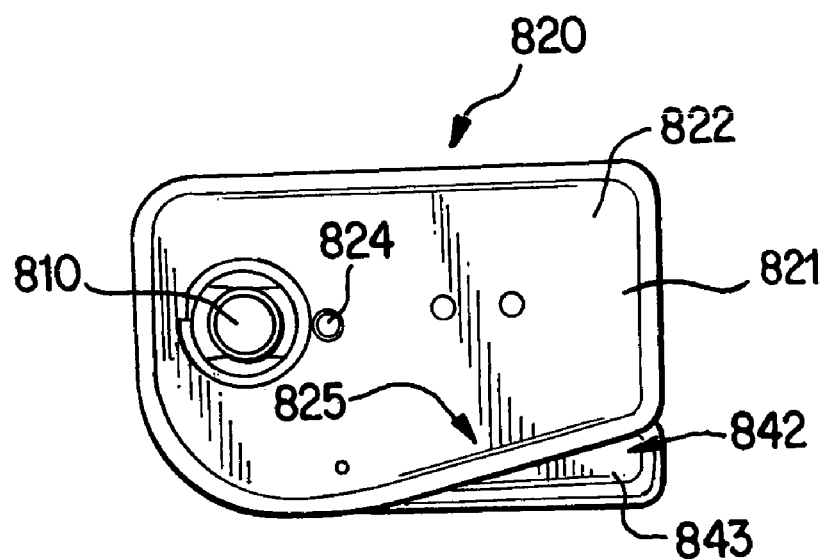
FIG. 34 is a top plan view of a trocar motor housing according to an alternative embodiment of the present invention.
Figure 35:
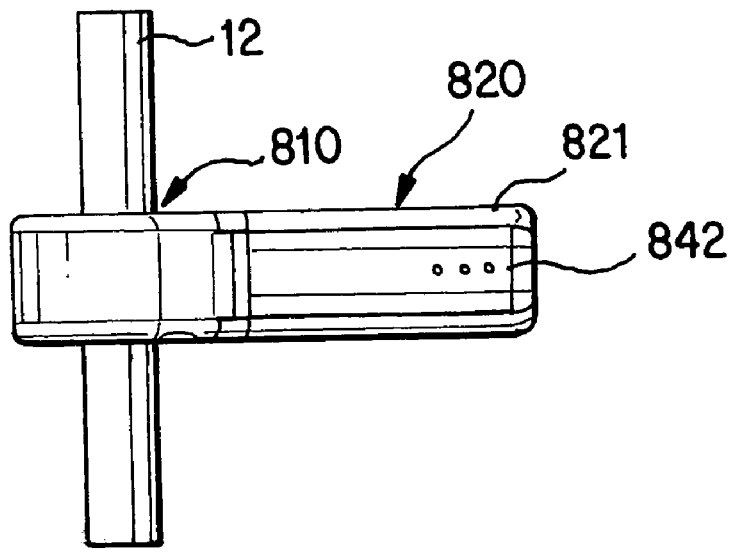
Figure 36:
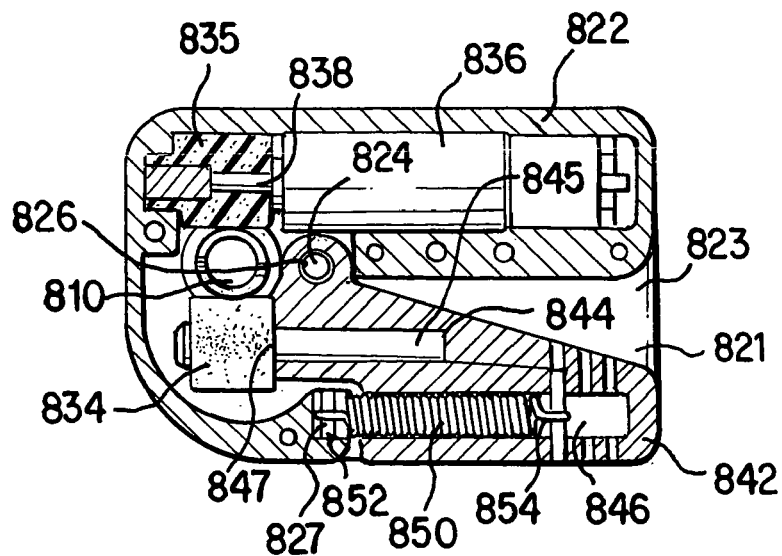
FIG. 36 is a schematic cross-sectional view of the trocar motor housing of FIG. 34 with a driven roller and pinch roller in position for driving an endoscopic instrument.
Figure 37:
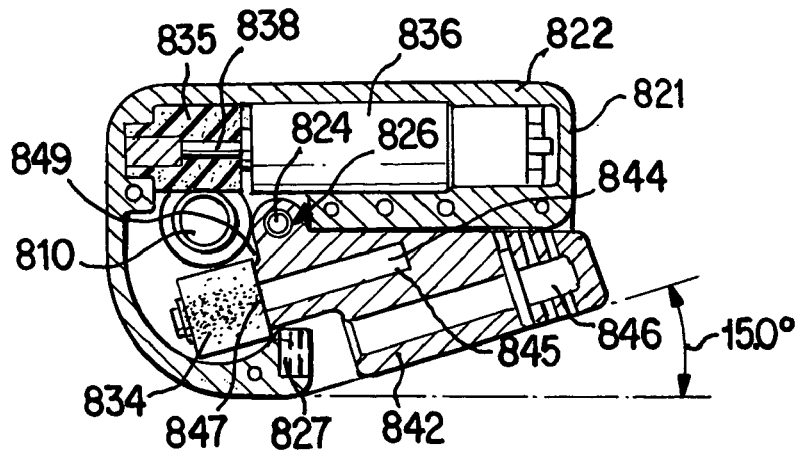
FIG. 37 is a schematic cross-sectional view of the trocar motor housing of FIG. 34 with the pinch roller of the motor housing being pivoted away the driven roller.

In this alternative embodiment, the housing 821 includes a first housing portion 822 with an internal space 823 that receives at least a part of a second housing portion 842 as shown in FIG. 36. The internal space 823 is sized to receive the second housing portion 842 so that the second housing portion 842 can move within and relative to the first housing portion 822. As illustrated in FIG. 34, the first housing portion 822 includes a tapered section 825 that exposes a portion 843 of the received second housing portion 842 so that an operator can simultaneously contact the first and second housing portions 822, 842 when she grasps the motor housing 821. The first housing portion 822 also includes a motor 836, such as that discussed above from Micro-Drives, and a drive shaft 838 extending from the motor 836. The drive roller 835 is secured to drive shaft 838 so that the drive roller 835 rotates in response to the movement of the drive shaft 838 in order to advance or retract the endoscopic instrument 12. The first housing portion 822 further includes a pin 824 that extends parallel to an inserted endoscopic instrument 12 as shown in FIGS. 36 and 37. The pin 824 forms a pivot point 826 about which the received second housing portion 842 pivots when the housing 821 is grasped and the second housing 842 is forced toward the motor 836.

A spring 850 extends between and connects the first and second housing portions 822 and 842 as illustrated in FIG. 36. The spring 850 includes a first end 852 securely positioned within an opening 827 in the first housing portion 822 and a second end 854 secured within an opening 846 in the second housing portion 842. Both ends 852, 854 of the spring 850 can be connected to their respective housing portions 822, 842 in a conventional manner. In a preferred embodiment, the ends 852, 854 of the spring 850 are secured around or through a cylindrical post that extends within a respective one of the openings 827, 846. In an alternative embodiment, the ends 852, 854 of the spring 850 are directly secured to a member within a respective one of the openings 827, 846 by welding, soldering, adhering or the like.

The second housing portion 842 includes an elongated shaft 844 having a first end 845 secured within an opening 846 and a second end 847 carrying the pinch roller 834. The pinch roller 834 is rotatably secured about the shaft 844 by a bearing as is known. Additionally, like the other rollers discussed herein, the rollers 834 and 835 include a resilient, friction covering material such as neoprene, rubber, etc. The roller 834 extends a distance away from a contoured edge 849 of the second housing portion 842 that is greater than the distance that the outer covering(s) of the roller 834 will compress so that the roller 834 can contact and apply pressure to the endoscopic instrument 12 without interference from the second housing portion 842.

In operation, the trocar housing 820 is grasped so that the second housing portion 842 moves relative to the first housing portion and into the internal space 823 to assume the position shown in FIG. 37. This movement of the second housing portion 842 causes the roller 834 to pivot away from the opening 810 and the driven roller 835. As a result, the endoscopic instrument 12 can be easily introduced into the housing 821 without having to overcome the friction created by a spring biased pinch roller 834. After the endoscopic instrument 12 has been positioned within the housing 821, the tension of the extended spring 850 causes the second housing portion 842 to pivot back toward the position shown in FIG. 36. The movement of the pinch roller 834 toward the position shown in FIG. 36 will be limited by the diameter of the endoscopic instrument 12. As a result, when the pinch roller pivots toward the driven roller 835, the pinch roller 834 is forced into engagement with the endoscopic instrument 12 so that it can cooperate with the driven roller 835 to move the endoscopic instrument 12 along the length of the trocar. The strength with which the pinch roller 834 engages the endoscopic instrument 12 can be adjusted by changing the length and/or spring constant of the spring 850. In an alternative embodiment, the driven roller 835 and the motor 836 can be positioned within the second housing portion 842 and the pinch roller 834 can be secured to a member extending into the first housing portion 822.

In any of the above-discussed embodiments, the motors or their output drive shafts can each include a well-known torque limiting device such as a well-known slip clutch. Each torque limiting device can be positioned within one of the motors. Alternatively, the torque limiting device can be positioned on an end of an output drive shaft between the motor and a driven gear. The toque limiting devices limit the amount of torque that can be applied to the body of the patient as the C-shaped arm 40 or any part of the C-shaped arm 40 is rotated relative to the body. As a result, body damaging torques are prevented from being applied to the body. Known slip clutches that can be used with the present invention are available from Stock Drive Products/Sterling Instruments.

While there have been shown and described and pointed out fundamental novel features of the present invention as applied to preferred embodiments thereof, it will be understood that various omissions and substitutions and changes in the form and details of the devices illustrated, and in their operation, may be made by those skilled in the art without departing from the spirit and scope of the invention as broadly disclosed herein. For example, chain or belt drives may be used in place of the above-described gears.

I claim:

1. An apparatus for moving a medical instrument in at least one direction, said apparatus comprising:

an elongated trocar and a drive assembly releasably secured to a trocar, said drive assembly comprising a housing including an opening for receiving the medical instrument, at least one motor, at least one drive roller operatively coupled to said motor, wherein the drive roller further comprises at least one pinch roller, and wherein said rollers each include an outer surface at least partially covered by a friction material, and wherein said friction material engages the medical instrument when the rollers move in response to the operation of said at least one motor.

2. An apparatus of claim 1 further including a spring that biases said pinch roller toward said drive roller.

3. An apparatus of claim 1 wherein said drive assembly includes a plurality of drive rollers and a plurality of pinch rollers.

4. An apparatus for moving a medical instrument in at least one direction, said apparatus comprising:

an elongated trocar and a drive assembly releasably secured to a trocar, said drive assembly comprising a housing including an opening for receiving the medical instrument, at least one motor, at least one drive roller operatively coupled to said motor, wherein said motor includes an output shaft coupled to said drive roller for rotating said drive roller, and wherein said drive roller rotates in a first direction for advancing the medical instrument into the trocar and in a second direction for retracting the medical instrument from within the trocar.

* * * * *